(12) United States Patent
Rosenthal et al.

(10) Patent No.: US 12,245,751 B2
(45) Date of Patent: Mar. 11, 2025

(54) METHOD FOR ADVANCED NERVOUS TISSUE IMAGING SYSTEM

(71) Applicant: Axon Imaging, Inc., Miami, FL (US)

(72) Inventors: Raul J. Rosenthal, Miami, FL (US); Fernando Dip, Buenos Aires (AR)

( * ) Notice: Subject to any disclaimer, the term of this patent is extended or adjusted under 35 U.S.C. 154(b) by 0 days.

(21) Appl. No.: 18/467,006

(22) Filed: Sep. 14, 2023

(65) Prior Publication Data
US 2024/0000301 A1    Jan. 4, 2024

Related U.S. Application Data

(63) Continuation of application No. 17/678,668, filed on Feb. 23, 2022, now Pat. No. 11,839,361, which is a
(Continued)

(51) Int. Cl.
*A61B 1/04* (2006.01)
*A61B 1/00* (2006.01)
(Continued)

(52) U.S. Cl.
CPC .......... *A61B 1/043* (2013.01); *A61B 1/00045* (2013.01); *A61B 1/0638* (2013.01);
(Continued)

(58) Field of Classification Search
None
See application file for complete search history.

(56) References Cited

U.S. PATENT DOCUMENTS

| | | | | |
|---|---|---|---|---|
| 4,253,470 A | * | 3/1981 | Sheingorn | A61B 3/00 351/243 |
| 4,532,918 A | * | 8/1985 | Wheeler | A61B 1/0646 348/69 |

(Continued)

FOREIGN PATENT DOCUMENTS

| | | |
|---|---|---|
| WO | 2010137739 A1 | 12/2010 |
| WO | 20200148726 A1 | 7/2020 |

OTHER PUBLICATIONS

International Search Report for PCT International Application No. PCT/US2020/054457 issued on Mar. 31, 2021.
(Continued)

*Primary Examiner* — John P Leubecker
*Assistant Examiner* — Jae Woo
(74) *Attorney, Agent, or Firm* — Jose Gutman; Fleit Intellectual Property Law

(57) ABSTRACT

A nervous tissue imaging system and a method therefor. The system includes: a housing containing an excitation light source, optically coupled with a source optical train, the excitation light source emits excitation light in a first wavelength range, which can be in a near ultraviolet light range, to illuminate a tissue region of interest including healthy nervous tissue and healthy non-nervous tissue. The excitation light in the first wavelength range causes the healthy nervous tissue, in response to being illuminated with the excitation light, to endogenously autoflouresce and emit first autofluorescence light at a first luminance in a second wavelength range. The healthy non-nervous tissue, in response to being illuminated with the excitation light, either avoids emitting any autofluorescence light in the second wavelength range; or endogenously autoflouresces and emits second autofluorescence light in the second wavelength range at a second luminance that is lower than the first luminance.

16 Claims, 20 Drawing Sheets

Related U.S. Application Data continuation of application No. PCT/US2021/041113, filed on Jul. 9, 2021, and a continuation of application No. PCT/US2020/054457, filed on Oct. 6, 2020.

(60) Provisional application No. 63/087,568, filed on Oct. 5, 2020, provisional application No. 63/050,018, filed on Jul. 9, 2020.

(51) Int. Cl.
  *A61B 1/06* (2006.01)
  *A61B 1/313* (2006.01)
  *A61B 5/00* (2006.01)

(52) U.S. Cl.
  CPC .......... *A61B 1/0646* (2013.01); *A61B 1/0655* (2022.02); *A61B 1/313* (2013.01); *A61B 5/0071* (2013.01); *A61B 5/0077* (2013.01); *A61B 5/4041* (2013.01)

(56) References Cited

U.S. PATENT DOCUMENTS

| | | | |
|---|---|---|---|
| 5,749,830 A | | 5/1998 | Kaneko et al. |
| 2002/0035330 A1* | | 3/2002 | Cline ............ A61B 1/045 |
| | | | 600/478 |
| 2002/0161282 A1* | | 10/2002 | Fulghum .......... A61B 1/07 |
| | | | 600/178 |
| 2004/0006276 A1* | | 1/2004 | Demos ............ A61B 1/063 |
| | | | 600/476 |
| 2006/0089554 A1* | | 4/2006 | Ishihara .......... A61B 1/043 |
| | | | 600/476 |
| 2009/0155803 A1 | | 6/2009 | Cohen et al. |
| 2014/0171764 A1 | | 6/2014 | Mikhailovna et al. |
| 2015/0094600 A1* | | 4/2015 | Grutzendler ........ A61B 5/0068 |
| | | | 600/476 |
| 2015/0099979 A1 | | 4/2015 | Caves et al. |
| 2015/0196193 A1* | | 7/2015 | Kienzle .......... A61B 1/00114 |
| | | | 600/109 |
| 2017/0105623 A1 | | 4/2017 | Mahadevan-Jansen et al. |
| 2017/0284938 A1* | | 10/2017 | Takimoto .......... A61B 5/0071 |
| 2018/0042482 A1 | | 2/2018 | Stepp et al. |
| 2018/0120230 A1 | | 5/2018 | Hiroyuki et al. |
| 2019/0209015 A1* | | 7/2019 | Liang ............ A61B 90/361 |
| 2022/0175229 A1 | | 6/2022 | Dip et al. |

OTHER PUBLICATIONS

Written Opinion of the International Searching Authority for PCT International Application No. PCT/US2020/054457 issued on Mar. 31, 2021.

International Search Report for PCT International Application No. PCT/US2021/041113 issued on Oct. 26, 2021.

Written Opinion of the International Searching Authority for PCT International Application No. PCT/US2021/041113 issued on Oct. 26, 2021.

\* cited by examiner $f_w$ = white
$f_{il}$ = illumination
$f_{ex}$ = excitation
$f_{fl}$ = fluorescence

| EXAMPLE EMBODIMENTS | FILTERS | | |
| --- | --- | --- | --- |
| | F1 | F2 | F3 |
| 1 | $f_w + f_{fl}$ | $f_{ex}$ | $f_w$ |
| 2 | $f_{il}$ | $f_{ex}$ | $f_w$ |

$f_{fl}$ = NOTCH FILTER (433 NM - 450 NM)
(REMOVES FLUORESCENCE LIGHT WAVELENGTHS $f_w$ = LONG PASS FILTER (400 NM - 1200 NM)
(REMOVES NEAR UV EXCITATION LIGHT WAVELENGTHS)

$f_{il}$ = LONG PASS FILTER (460 NM - 1200 NM)
(REMOVES NEAR UV EXCITATION LIGHT WAVELENGTHS
AND REMOVES FLUORESCENCE LIGHT WAVELENGTHS)

$f_{ex}$ = BAND PASS FILTER (382 NM - 392 NM)
(PASSES ONLY NEAR UV EXCITATION LIGHT WAVELENGTHS)

FIG. 14

METHOD FOR ADVANCED NERVOUS TISSUE IMAGING SYSTEM

CROSS-REFERENCE TO RELATED APPLICATIONS

This application is based upon and claims priority from prior U.S. Provisional Patent Application No. 63/050,018, filed on Jul. 9, 2020, and from prior U.S. Provisional Patent Application No. 63/087,568, filed on Oct. 5, 2020, and from prior PCT Patent Application PCT/US2020/054457, filed on Oct. 6, 2020, and from prior PCT Patent Application PCT/US2021/041113, filed on Jul. 9, 2021, and from pending U.S. patent application Ser. No. 17/678,668, filed on Feb. 23, 2022, the collective entire disclosure of which is herein incorporated by reference in its entirety.

BACKGROUND

The present disclosure generally relates to systems, devices, and methods for tissue imaging. More particularly, a disclosed tissue imaging system and related methods are suitable for use with tissue under examination including both nervous tissue and non-nervous healthy tissue (e.g., non-cancerous and non-pathologic tissue), whether in vivo or ex vivo, to identify and visually image the nervous tissue contrasted from the non-nervous healthy tissue based on autofluorescence of the nervous tissue by excitation with electromagnetic radiation.

Despite numerous major advancements in surgical techniques and equipment over recent decades, surgery continues to be linked to an unacceptably high number of iatrogenic injuries. In some instances, advanced surgical techniques, like minimally-invasive and robotic surgery, appear to have actually increased the risk of certain injuries. Among these injuries, iatrogenic injuries to nerves and other nervous tissues such as duramadre are among the most catastrophic, placing patients at risk for both short and long-term disabling motor and sensory deficits. They also are disturbingly common, documented in up to twenty percent (20%) of patients undergoing certain common procedures like thyroidectomies, parotidectomies, resection of breast and colon cancers, prostatectomies, and inguinal hernia repairs. Avoiding unintentional nerve damage, or recognizing an injury in order for it to be repaired at the time of surgery, during operative procedures requires that nerves and nervous tissues be identified accurately and dissected carefully, both challenging undertakings when standard visualization techniques are used. Consequently, the ability to accurately identify sensory and motor nerves, as well as duramadre, during surgical procedures is crucial to prevent injury.

Clear and reliable visualization of peripheral nerves and duramadre as distinguishing/contrasting those from surrounding normal, non-nervous healthy tissue (e.g., non-cancerous and non-pathologic tissue) is highly desirable when performing operations in many areas of the human body. Current nerve-sparing techniques have a rate of success that is dependent upon the type of operation, the disease process being treated, and the surgeon's experience and training. Iatrogenic injury to peripheral motor and sensory nerves, as well as to central nervous tissue such as duramadre, causes impairment resulting reduced quality of life for patients and creates significant burdens to the healthcare system. Despite surgeons' extensive academic and practical training, and irrespective of years of experience, however, iatrogenic nerve damage may also occur because anatomical variations and the presence of pathology can hamper recognition of critical anatomical structures. A means to enhance recognition of peripheral nerves within the surgical field could prevent many such injuries.

Tools like electrical stimulation devices possess an unknown level of accuracy and cannot identify sensory nerves or the duramadre. The use of imaging tools like computed tomography (CT) and magnetic resonance imaging (MRI) as intraoperative guides is problematic because of time latency of interpretation between the radiological image and the human tissue visualization with white light during surgery which further increases the probability of inaccuracies.

Fluorescent imaging techniques, in conjunction with special fluorescent dyes/probes that are armed with antibodies that attach indiscriminately to nerves, have proven successful in preclinical and clinical studies at helping surgeons identify peripheral nerves and/or duramadre intraoperatively. However, the labeling of tissues of interest by administering or applying to patients extrinsic or exogenous fluorophores, such as fluorescent agents, fluorescent dyes, fluorescent markers, or fluorescent tissue probes, such as to label peripheral nerves, is problematic. Most fluorescent tissue probes and fluorescent dyes have not been shown to be safe and effective; their long term effects after attaching to nerves are unpredictable and consequently they generally are not approved by the United States Food and Drug Administration ("FDA"). A few fluorescent dyes have been approved for clinical use, but most require extensive preparation times, are costly, must be used in limited doses to mitigate toxicity, have short half-lives in vivo, may cause serious or even fatal allergic reactions, and require precise timing of administration. Despite the above mentioned potential for unpredictable side effects, if fluorescent markers or fluorescent dyes are not highly specific for neural tissue (also referred to as nervous tissue), they can actually obscure a peripheral nerve by also enhancing surrounding non-neural tissue (non-nervous tissue), making peripheral nerve and/or duramadre visualization even more difficult. Nonspecific or competitive binding of the extrinsic or exogenous fluorophores to nervous tissue and/or surrounding non-nervous tissue may result in poor signal-to-background ratio and/or limited dynamic range when attempting to detect a tissue of interest. Additionally, observed differences in fluorescence between tissues following administration of a fluorescent dye or fluorescent marker may be the result of differences in tissue perfusion rather than differential uptake by different tissue types. Arteries perfusing peripheral nerves are very small compared with arteries perfusing other anatomic structures, which may accentuate differences in fluorescence arising from differential perfusion.

For at least the foregoing issues, the administration or application of extrinsic or exogenous fluorophores, such as fluorescent agents, fluorescent dyes, fluorescent markers, and fluorescent tissue probes, to label tissues of interest, such as for intraoperative identification of peripheral nerves and/or duramadre, gives inconsistent and unreliable results.

Because of these and other problems, there is a need for improved visual imaging of tissue; particularly, peripheral nerves and duramadre, that does not require fluorescent dyes, fluorescent tissue probes, or other fluorescent markers, to increase visual contrast between the nerve/duramadre and non-nervous tissue surrounding the nerve/duramadre. This needed visual contrast would allow for clear intraoperative visualization of nerves/duramadre while simultaneously eliminating increased patient risk associated with the administration of, for example, chemical markers or dyes to the patient.

Therefore a need exists to overcome the problems with the prior art as discussed above.

BRIEF SUMMARY

A nervous tissue imaging system and a method therefor are disclosed. The system includes: a housing containing an excitation light source, optically coupled with a source optical train, the excitation light source emits excitation light in a first wavelength range in a near ultraviolet light range to illuminate a tissue region of interest including healthy nervous tissue and healthy non-nervous tissue. The excitation light is in a first wavelength range that causes the healthy nervous tissue, in response to being illuminated with the excitation light, to endogenously autoflouresce and emit first autofluorescence light at a first luminance in a second wavelength range. The healthy non-nervous tissue, in response to being illuminated with the excitation light, either avoids emitting any autofluorescence light in the second wavelength range; or endogenously autoflouresces and emits second autofluorescence light in the second wavelength range at a second luminance that is lower than the first luminance. In certain embodiments the second luminance is lower than about 50% of the first luminance.

The method includes illuminating an excitation light in a first wavelength range in a near ultraviolet light range onto a tissue region of interest including healthy nervous tissue and healthy non-nervous tissue. The method captures, with a camera, image data of endogenous autofluorescence light emitted from the healthy nervous tissue at a first luminance in a second wavelength range in a visible light range. The method captures, with the camera, image data of light signal received from the healthy non-nervous tissue contemporaneous with capturing the image data of the endogenous autofluorescence light emitted from the healthy nervous tissue at the first luminance in the second wavelength range, the healthy non-nervous tissue, in response to being illuminated with the excitation light, at least one of: avoids endogenously autoflourescing and emitting any autofluorescence light in the second wavelength range; or endogenously autoflouresces and emits second autofluorescence light in the second wavelength range at a second luminance that is lower than the first luminance. In certain embodiments the second luminance is lower than about 50% of the first luminance. The method forms a first image of the healthy nervous tissue in the tissue region of interest and a second image of the healthy non-nervous tissue in the tissue region of interest. The method displays the first image and the second image on a display, with the first image being contrasted (distinguished) from the second image to identify the location of nervous tissue and the location of the non-nervous tissue in the tissue region of interest.

BRIEF DESCRIPTION OF THE DRAWINGS

The accompanying figures in which like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which:

FIG. 14 is a table illustrating filter parameters suitable for use in two example embodiments of a tissue imaging system;

DETAILED DESCRIPTION

Figure 1:
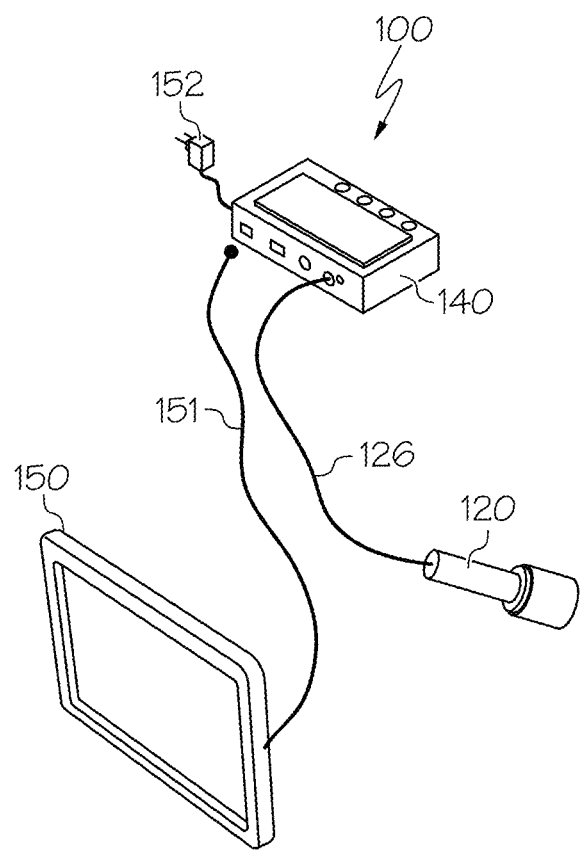
FIG. 1 is an illustration of an example of a tissue imaging system, according to various embodiments of the invention.

As required, detailed embodiments are disclosed herein; however, it is to be understood that the disclosed embodiments are merely examples and that the devices, systems and methods described herein can be embodied in various forms. Therefore, specific structural and functional details disclosed herein are not to be interpreted as limiting, but merely as a basis for the claims and as a representative basis for teaching one of ordinary skill in the art to variously employ the disclosed subject matter in virtually any proprietary detailed structure and function. Further, the terms and phrases used herein are not intended to be limiting, but rather, to provide an understandable description. Additionally, unless otherwise specifically expressed or clearly understood from the context of use, a term as used herein describes the singular and/or the plural of that term.

INTRODUCTION

The ability to identify nerves/duramadre accurately and, thereby, dissect them safely must be considered a high priority of surgeons. It is also of critical importance to detect and repair a nerve/duramadre if injured during a procedure. Most, if not all, critical, structural tissue disruption and nerve/duramadre injury occurs in the operative setting. A surgeon's knowledge of complex anatomical structures and use of standard visual aids is often insufficient to avoid such injuries, regardless of the surgeon's level of expertise. Nerve axonal/duramadre injury, including traction and partial or complete transection, is a significant, common complication associated with a variety of surgical procedures. Such surgical procedures include, but are not limited to, surgery of the brain, spine, colonic resections, thyroidectomies, parathyroidectomies, parotidectomies, coronary artery bypass graft (CABG), groin hernia repairs, open heart surgeries, and breast cancer surgery, affecting up to 20% of patients. Although the majority of iatrogenic neuropathies that result from operative injury resolve with conservative management and physiotherapy, some cause prolonged or permanent impairment.

Despite the potential value of using various fluorescent dyes, fluorescent markers, and fluorescent tissue probes to image nerves, tissue endogenous autofluorescence has the distinct advantage of providing real-time imaging without the need for invasive techniques or patient exposure to potentially unsafe compounds. Moreover, the fluorescent dyes and fluorescent tissue probes utilized in most of the research conducted thus far on nerve identification are often difficult to procure. And they all depend on the blood flow to the region that might be compromised by local (blood clots) or systemic disease (atherosclerosis).

The inventors believe they are the first to study nerve/peripheral nerve/duramadre endogenous autofluorescence in humans during a surgical procedure and to develop corresponding technology leveraging autofluorescence in the operating room to prevent or reduce the risk as well as recognize and repair iatrogenic intraoperative nerve/peripheral nerve/duramadre injury. Various embodiments of the disclosed invention allow for enhanced, real-time intraoperative visualization of nervous tissue, which can include any type of nerves/peripheral nerves/duramadre, by causing and imaging nervous tissue (any nerve/peripheral nerve/duramadre) endogenous autofluorescence using different intensities and wavelengths of electromagnetic radiation coupled with different wavelength range-pass optical filters by an integrated tissue imaging system of devices configured for operating room use. Nervous tissue endogenous autofluorescence, according to various embodiments, is induced or elicited by illumination of a tissue region of interest (under examination) with radiation of an excitation electromagnetic signal (which also may be referred to as an excitation light, excitation light signal, and the like), and without the use of any fluorescent marker, fluorescent tissue probe, or fluorescent dye, to emit the fluorescence signal (which also may be referred to as a fluorescence light, fluorescence light signal, and the like). Additionally, the inventors' findings suggest that use of light wavelength filters, particularly optical filters that selectively transmit excitation light in the near-ultraviolet (NUV) range and bandpass optical filters to largely remove reflected light (and also remove other possible interfering radiated electromagnetic signals) from nervous tissue emitted fluorescence light increase perceived levels of nerve/duramadre autofluorescence, thereby increasing visual contrast of nervous tissue from surrounding non-nervous tissue. Various embodiments of the disclosed invention are a means of altering the rate and severity of iatrogenic nervous tissue injury in clinical surgical practice.

A system for imaging tissue is described herein. In some embodiments, the tissue imaging system is used specifically to enhance and facilitate intraoperative visualization of nerves/peripheral nerves/duramadre by the operating surgeon.

As used herein, the terms "tissue imaging system", "nervous tissue imaging system", and "nerve/duramadre imaging system" are intended to mean a system comprised of devices and components utilized to enhance visualization of specific tissue structures, such as peripheral nerves/duramadre, for example, from surrounding healthy non pathologic nor cancerous tissues. It is to be understood, however, that a nerve/duramadre imaging system may, in some embodiments, be used to visualize non-neural structures or tissues.

As used herein, a "medical device" is an instrument, apparatus, implement, machine, appliance, software, material, or other similar or related article intended to be used, alone or in combination for human beings for the specific medical purposes of diagnosis, prevention, monitoring, treatment or alleviation of disease.

As used herein, a "peripheral nerve" is a motor, sensory, autonomic, or mixed-function nerve existing outside of the brain or spinal cord proper. For the purposes of this disclosure, "peripheral nerve" includes cranial nerves outside of the dura enclosing the brain. "Peripheral nerve" also includes mixed spinal nerves and spinal ganglia, whether outside of or enclosed by the spinal dura (thecal sac). Some non-limiting examples of "peripheral nerves" include the facial nerve and its branches, the superior laryngeal nerve, the recurrent laryngeal nerve, the hypoglossal nerve, the spinal accessory nerve, nerve roots, nerve trunks, and nerve branches of the brachial plexus and the lumbar plexus, the long thoracic nerve, the medial and lateral pectoral nerves, sympathetic ganglia, pelvic sensory nerves, and many others. As used herein, "spinal dura", "dura", "duramadre", or "thecal sac" is the thick, dense, fibrous membranous structure surrounding the spinal cord, dorsal and ventral spinal nerves, and dorsal spinal ganglia.

As used herein, "wavelength," or "wavelengths" means a specific wavelength (or range of wavelengths) of an electromagnetic radiation, whether visible or invisible to the human eye, including near-ultraviolet light, ultraviolet light, near-infrared light, or infrared light. "Wavelength" may represent a range of wavelengths. The range of wavelengths may be discreet and continuous or may be discontinuous.

As used herein, "emitted light" means electromagnetic radiation of a discrete wavelength or range of wavelengths emitted by a cell, a tissue, or an anatomic structure in response to illumination or irradiation with electromagnetic radiation of a different wavelength or range of wavelengths. "Emitted light" originates solely from the cell, tissue, or anatomic structure and does not comprise reflected excitation light or light reflected from other sources of ambient light. "Emitted light" arises as a consequence of an intrinsic property of the atoms, molecules, or a particular arrangement of atoms and molecules forming the cell, the tissue, or the anatomic structure.

As used herein, "excitation light" means electromagnetic radiation used to illuminate or irradiate a cell, a tissue, or an anatomic structure to cause the cell, the tissue, or the anatomic structure to generate an emitted light comprising a different wavelength or range of wavelengths than the excitation light.

As used herein, a "low-pass filter", which may also be referred to as a "long pass filter", means a low-pass (long pass) wavelength optical filter, including a digital filter that passes electromagnetic radiation having a wavelength longer than a selected cutoff wavelength. A "low-pass filter" ("long pass filter") may comprise a single optical filter element or a plurality of optical filter elements configured to allow passage of electromagnetic radiation having a wavelength longer than the selected cutoff wavelength.

Correspondingly, a "high-pass filter", which may also be referred to as a "short pass filter", means a high-pass (short pass) wavelength optical filter, including a digital filter that passes electromagnetic radiation having a wavelength shorter than a selected cutoff wavelength. A "high-pass filter" ("short pass filter") may comprise a single optical filter element or a plurality of optical filter elements configured to allow passage of electromagnetic radiation having a wavelength shorter than the selected cutoff wavelength.

Also as used herein, a "band-pass filter" means a band-pass wavelength optical filter, including a digital filter that passes electromagnetic radiation having a range of wavelengths within a selected discrete range of wavelengths between a first wavelength and a second wavelength longer than the first wavelength. A "band-pass filter" may comprise a single optical filter element or a plurality of optical filter elements configured to allow passage of electromagnetic radiation having a range of wavelengths within the selected range of wavelengths.

As used herein, "reflected light" means excitation light and/or other illumination light such as ambient light, white light, and the like, passing into a receiving optical train after being reflected from a tissue, a surface, or the like. "Reflected light" is not "emitted light" as "emitted light" is separately defined herein.

As used herein, "nervous tissue" is intended to mean tissue that includes one or more of nerves, peripheral nerves, duramadre, and central nervous system tissue including a nerve.

As used herein, "healthy nervous tissue" is intended to mean nervous tissue, as defined herein, that is non-cancerous and non-pathologic tissue.

As used herein, "non-nervous tissue" is intended to mean any biological tissue, whether human or animal, that is not nervous tissue, as defined herein.

As used herein, "healthy non-nervous tissue" is intended to mean non-nervous tissue, as defined herein, that is non-cancerous and non-pathologic tissue.

Overview of Example Tissue Imaging System

The example tissue imaging system can be used by healthcare professionals in a clinical setting, for example, a hospital, an ambulatory surgical center, and the like. In some embodiments, a surgeon or healthcare practitioner may use the tissue imaging system in combination with additional imaging devices, such as ultrasound, fluoroscopy, or other conventional imaging devices. The tissue imaging device, standing alone or used with such other imaging devices, may be used, in some embodiments, to help a surgeon distinguish nervous tissue from other anatomical structures and surrounding non-nervous tissue, decreasing the risk of injury to a nervous tissue such as a nerve/peripheral nerve/duramadre. In some embodiments, the tissue imaging device is structurally adapted for use integrated with an operating microscope, a rigid or flexible endoscope, laparoscopes, thoracoscopes, and related devices; end-effector instruments such as instruments used in minimally invasive surgical procedures throughout the body, surgical instruments used during traditional "open" procedures, or other medical devices with which integration of the medical device with a tissue imaging system is advantageous or desirable.

No fluorescent markers, fluorescent tissue probes, or fluorescent dyes are used in nervous tissue. The tissue imaging system creates a visual image of a target tissue, such as a peripheral nerve/duramadre, by causing the target tissue to fluoresce in response to illumination with light, whether visible outside the range of visible light. Tissue fluorescence occurs without use of adjunctive chemical or pharmacologic compositions, such as fluorescent dyes, fluorescent markers, fluorescent tissue probes, or the like, whether applied topically or administered (orally or parenterally). Typically, nervous tissue, such as peripheral nerves, fluoresce intrinsically upon illumination with excitation light differently than surrounding healthy non-nervous tissue, e.g., normal/non pathologic/non-cancerous tissues, depending on the wavelength and intensity of the excitation light, light filtering means, and image processing techniques. The system exploits contrasting levels of fluorescence to distinguish nervous tissue, such as peripheral nerves/duramadre, from surrounding non-nervous tissue, and particularly from healthy non-nervous tissue.

Significant aspects of such a tissue imaging system include a means for illuminating a tissue bed, such as a surgical field, with at least an excitation light and optionally also with an illumination light. According to various embodiments, a target tissue region of interest, includes a nervous tissue such as a nerve/peripheral nerve/duramadre, which endogenously autofluoresces in response to the incident excitation light at an intensity (luminance) higher in a wavelength range in the visible light range and different from autofluorescence (if any) of adjacent and/or surrounding background non-nervous tissue in the tissue region of interest, and from reflected light, if any, for the tissue region of interest. A camera (which may also be referred to herein as a "Dendrite camera"), or similar sensor/detector receives the tissue-emitted fluorescence light, and possibly reflected light from the tissue region of interest, and the light signals are processed, such as to create a visual image of the tissue region of interest for display. The visual image includes a first image 802 of healthy nervous tissue which is highlighted by the tissue imaging system, such as in bright white or other color (see for example image 802 in FIG. 8) and a second image 804 of healthy non-nervous tissue (see for example image 804 in FIG. 8, which is a much darker image contrasted from the highlighted image 802 in FIG. 8) which is adjacent to and/or surrounding the first image of the nervous tissue in the tissue region of interest. This visual image of the tissue region of interest, such as for display on a display screen, includes the first image and the second image, and shows by contrast imaging between the first image and the second image the location of healthy nervous tissue relative to adjacent and/or surrounding healthy non-nervous tissue. This visual image can provide significant information assisting, for example, a surgeon to perform surgical procedures on a patient.

In summary, an example nervous tissue imaging system can include a housing configured for use in a sterile environment, where the housing contains an excitation light source, optically coupled with a source optical train, the excitation light source configured to selectively control and emit, from the excitation light source and coupled through the source optical train, excitation light in a first wavelength range to illuminate a tissue region of interest including healthy nervous tissue and healthy non-nervous tissue. In certain embodiments the first wavelength range is in a near ultraviolet light range. The excitation light source is designed and constructed to emit the first wavelength range of the excitation light that causes the healthy nervous tissue, in response to being illuminated with the excitation light, to endogenously autoflouresce and emit first autofluorescence light at a first luminance (intensity) in a second wavelength range in a visible light range. Further, the healthy non-nervous tissue, in response to being illuminated with the excitation light, at least one of: avoids endogenously autoflourescing and emitting any autofluorescence light in the second wavelength range; or endogenously autoflouresces and emits second autofluorescence light in the second wavelength range at a second luminance (intensity) that is lower than the first luminance. In certain embodiments the second luminance is lower than about 50% of the first luminance. Control electronic circuitry, electrically coupled with the excitation light source, controls the excitation light source. A controller/processor, operatively coupled with the control electronic circuitry and with the excitation light source, is configured to selectively control at least one operational parameter of the excitation light source that controls the excitation light from the excitation light source.

The tissue imaging system may include additional elements as discussed herein below.

The excitation light illuminating the tissue bed comprises a wavelength or a range of wavelengths, or intervals over a range of wavelengths (collectively referred to herein as "wavelength(s)", that cause an intrinsic effect of the biochemical structure of the tissue, such as nervous tissue. This intrinsic effect causes the tissue (e.g., nervous tissue) to emit fluorescence light at a particular range of wavelengths that is different (typically longer wavelengths) relative to the range of wavelength(s) (typically shorter wavelengths) of the excitation light. The tissue imaging system captures the wavelength or wavelengths of light emitted from the nervous tissue in response to the nervous tissue endogenous autofluorescence effects or other intrinsic properties which are induced or elicited by illumination of the excitation light on the nervous tissue.

Some embodiments of the tissue imaging system comprise a data processor and a software package residing on a memory. The software package directs an excitation light source via the data processor to emit light onto or into a patient's body at a particular wavelength or range of wavelengths. In response to the emitted excitation light, tissues emit light at a particular wavelength or in a particular wavelength region. The wavelength and intensity of the emitted light is intrinsic to the particular tissue type and structure. More specifically, a nervous tissue, such as a nerve/peripheral nerve/duramadre comprising nerve tissue, when stimulated or excited, emits (e.g., autofluoresces) an intrinsic and particular wavelength or range of wavelengths of light (hereinafter, "emitted light"). Such emitted light may be due to fluorescence ("fluorescence light"), other phenomenon, or fluorescence in combination with other phenomenon. The tissue imaging system, such as a nerve/duramadre imaging system, receives light from the illuminated tissue (tissue region of interest) and, in some embodiments, filters it with a detection filter to identify at least a healthy nervous tissue, such as a nerve/duramadre, emitted light, contrasted to adjacent and/or surrounding healthy non-nervous tissue emitted light or reflected light, and to generate a corresponding data signal. The data signals representing an image of the nervous tissue, e.g., nerve/duramadre, emitted light, which is contrasted to a background image of adjacent and/or surrounding healthy non-nervous tissue emitted light or reflected light, is transmitted to an image display for visualization by the user.

Full details of a tissue imaging system are provided by the written disclosures and several drawing figures herein.

Discussion of Examples of Tissue Imaging System and Related Component Devices

FIG. 1 is an illustration of an example of a tissue imaging system 100, according to various embodiments. FIG. 1 shows a tissue-imaging system 100. Tissue imaging system 100, in some embodiments, is a nerve tissue imaging system configured for intraoperative imaging of peripheral nerves. System 100 comprises various component devices for generating an excitation light and directing this to illuminate a tissue region of interest thought to contain a nerve/peripheral nerve/duramadre. In some embodiments, the system 100 includes various components for generating an illumination light (e.g., white light or "approximate" white light) which might illuminate the relevant structures and tissue in the tissue region of interest.

In response to illumination of the tissue region of interest, containing a nerve/peripheral nerve/duramadre therein, with excitation light, at least two different types of light (electromagnetic radiated signal) are created: (1) reflected light, which may include excitation light reflected by non-nervous tissue and by nervous tissue (e.g., the nerve/peripheral nerve/duramadre) in the tissue region of interest; and (2) emitted light, which is light (electromagnetic radiated signal) emitted by the nervous tissue (e.g., the nerve/peripheral nerve/duramadre) or possibly emitted by other non-nervous tissue, via fluorescence or other intrinsic property in response to radiated energy received by the excitation light illuminating the tissue region of interest.

In response to illumination of the tissue region of interest, containing a nerve/peripheral nerve/duramadre therein, with illumination light, at least two different types of light (electromagnetic radiated signal) might be created: (1) reflected illumination light reflected by nervous tissue and non-nervous tissue in the tissue region of interest; and (2) possible emitted light, which is light (electromagnetic radiated signal) emitted by the non-nervous tissue via fluorescence or other intrinsic property in response to radiated energy received by the illumination light illuminating the tissue region of interest.

In some embodiments, an interrogation unit 120 (see also, for example, FIGS. 2 and 3) generates the excitation light and receives reflected and emitted light for imaging processing. In some embodiments, the interrogation unit 120 might generate, in addition to or in the alternative of the excitation light, the illumination light and receives reflected (and possibly emitted light) for image processing. Examples of this system and process will be discussed in more detail further below.

System 100 also includes a controller 140 housing components such as a processor 142 (see FIG. 4, for example) and a user interface 146, in some embodiments. In some embodiments, as in the example shown in FIG. 1, elements of system 100 are electrically and communicatively coupled to one another by cables, such as a first cable 126 and a second cable 151. In some embodiments, a power source 152 is electrically coupled to controller 140.

Figure 8:
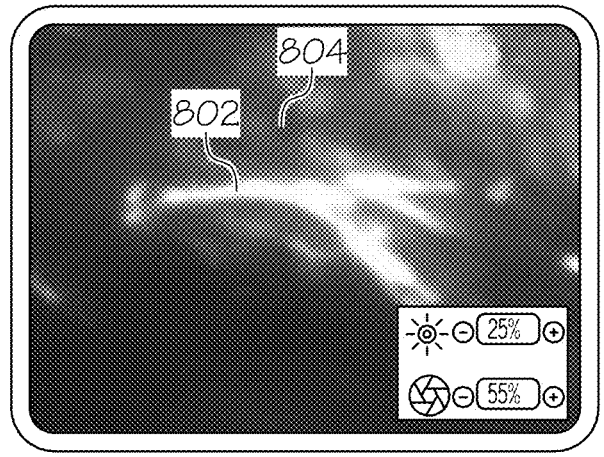
FIG. 8 is an illustration of an example video display of a tissue imaging system, according to various embodiments.

FIG. 1 also shows an image display 150, whereupon a user of the system 100 may visualize an image of the tissue region of interest being examined (tissue region under examination), which might show by contrast imaging the location of healthy nervous tissue contrasted with adjacent and/or surrounding healthy non-nervous tissue. See, for example, FIG. 8, illustrating an image display which is displaying formed images of healthy nervous tissue 802 (highlighted in bright white or other color in FIG. 8) contrasted from adjacent and/or surrounding healthy non-nervous tissue 804 (much darker image contrasted from the highlighted image 802 in FIG. 8).

The depiction of various devices forming the system 100 shown by FIG. 1 is by way of example only; additional configurations of interrogation device 120, controller 140, and image display 150 are within the scope of these disclosures and the teachings found herein. For example, in some embodiments and as shown in FIG. 1, first cable 125 communicatively and electrically couples interrogation device 120 with controller 140 and a second cable 151 communicatively and electrically couples image display 150 to the controller 140. This is only an example for illustration, and not meant to be limiting. In some embodiments, interrogation device 120 is "free-standing," having an internal power source and a wireless communication means of wirelessly exchanging instructions and data with controller 140. Similarly, image display 150, in some embodiments, comprises an internal or other separate power source and wireless communication means that can wirelessly communicate image data and other information with the controller 140.

Examples of an internal power source include a battery. The battery may be any battery suitable for use in a medical device, including a battery that is non-rechargeable and disposable, or a rechargeable battery. Some examples of medically suitable, non-rechargeable batteries include an alkaline battery, a lithium battery, a solid-state battery, and the like. In some embodiments, the battery is a rechargeable battery, such as a nickel-cadmium battery, nickel metal hydride battery, a nickel zinc battery, a lithium ion battery, or other suitable rechargeable energy storage device.

Embodiments of the system 100 not comprising the first cable 126 may have a wireless communication means wirelessly communicatively coupling interrogation unit 120 to the controller 140. Some embodiments of the system 100 not comprising the second cable 151 may have a wireless communication means wirelessly communicatively coupling image display 150 with controller 140.

Non-limiting examples of wireless communication means suitable for use in by various components of system 100 include transmitters and receivers using various wireless technologies well known in the art, including, for example, Bluetooth and WiFi wireless technology platforms.

Figure 2:
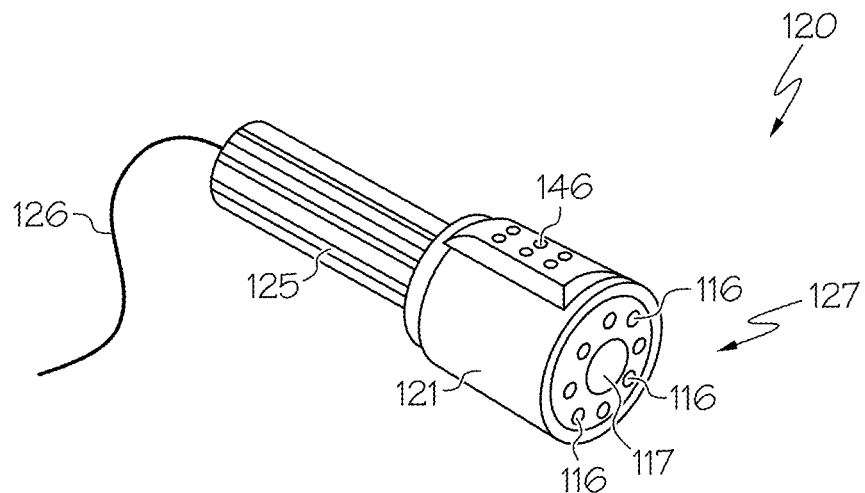
FIG. 2 is an illustration of an example interrogation unit suitable for use with the tissue imaging system of FIG. 1.
Figure 3:
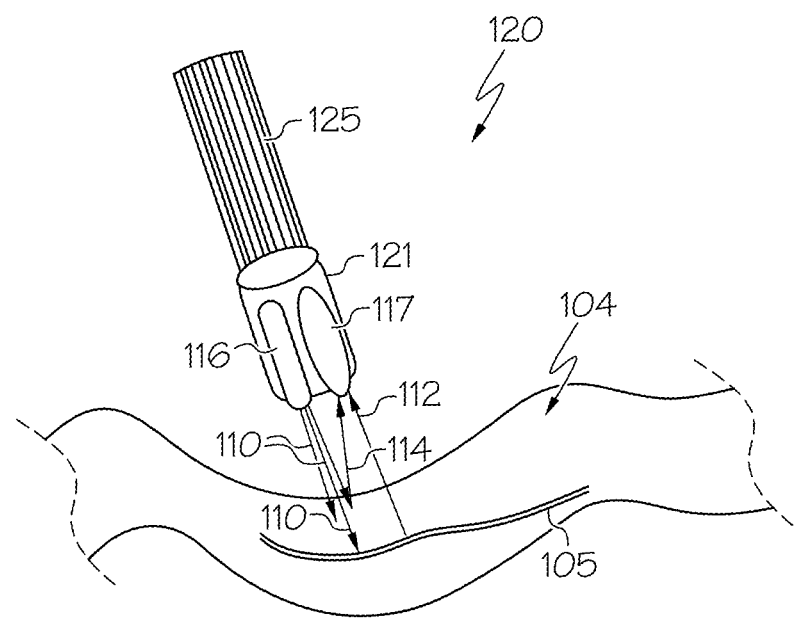
FIG. 3 is an illustration of a cutaway-side view of the example interrogation unit of FIG. 2, shown in an example examination of a tissue of interest containing a nervous tissue surrounded by non-nervous tissue.

FIG. 2 is an illustration of an embodiment of the interrogation unit 120 of the tissue imaging system 100. FIG. 3 is a side view of an embodiment of the interrogation unit 120 of the tissue imaging system 100. As in the embodiments shown in FIGS. 2 and 3, and in some other embodiments, interrogation unit 120 comprises a housing 121 configured to house electronic, optical, and related elements configured to provide tissue illumination and collection of light from the illuminated tissue region of interest. Housing 121 is formed from a medical grade material and configured for use in a sterile surgical environment. In some embodiments, housing 121 is configured for gas sterilization, such as using ethylene oxide, ozone, or other gases suitable for sterilizing sensitive electronic medical equipment that would be destroyed by heat-based sterilization systems and techniques. In some embodiments, housing 121 is not configured for sterilization but is used with a sterile disposable sac or equipment-condom is used that covers and at least partially encloses housing 121 wherein interrogation unit 120 may be used in a sterile operating-room environment. Elements contained within or coupled to housing 121 include, in some embodiments, an excitation light source 102, an illumination light source 103, a source optical train 116, a receiving optical train 117, a camera 122 (see FIG. 4), and a handle 125. In some embodiments, first cable 126 electrically, communicatively, or electrically and communicatively couples interrogation unit 120 to controller 140. Housing 121 may also contain additional elements, for example, mounting or fixation means, electronics, cooling means, thermal insulation, and the like, according to a particular embodiment or various embodiments of interrogation unit 120.

In some embodiments, interrogation unit 120 is arranged and configured as shown in FIGS. 2 and 3. Handle 125 is coupled to the housing 121 separate or generally opposite from a distal end 127, such that elements of source optical train 116 and receiving optical train 117 are not obscured from radiating and receiving light. Handle 125, in some embodiments, is a unitary body with housing 121. First cable 126 enters interrogation unit 120 via a handle 125, in some embodiments, to keep first cable 126 out of a line-of-sight between a distal end 127 and the tissue region of interest being illuminated and visualized. In some embodiments, source optical train 116 and receiving optical train 117 are arranged alongside one another within housing 121 in a configuration similar to that shown by FIG. 3. The depiction of source optical train 116 and receiving optical train 117 within housing 121 by FIG. 3 is diagrammatic and offered by example; other configurations of source optical train(s) 116 and receiving optical train(s) 117 are within the scope of the disclosures herein.

For example, in some embodiments of system 100, source optical train 117 is a plurality of source optical trains configured in an array or pattern, such as the circular pattern of eight (8) source optical trains 117 around a perimeter of distal end 127 shown by FIG. 2. In this, and other embodiments comprising an array of source optical trains 117, tissue region of interest 104 may be more brightly and evenly illuminated with excitation light 110. Bright and uniform illumination may reduce light shadowing effects allowing enhanced visualization of tissue region of interest 104 by system 100. Other and any number of arrangements, patterns, or arrays comprising any number of source optical trains 117, without limitation, are considered to be within the scope of this disclosure.

Excitation light source 102 (see FIG. 4) is located within housing 121, in some embodiments. Optionally, in certain embodiments, an illumination light source 103 (see FIG. 4) is located within housing 121. In some embodiments, the illumination light source 103 comprises a wide electromagnetic radiated signal wavelength-range "white" light (or approximately white light) source, such as a halogen (xenon) lamp, a 450-Watt xenon lamp, a tungsten-halogen lamp, a mercury arc lamp, or the like, for example. In certain embodiments, the illumination light emitted from the illumination light source 103 may be coupled through one or more optical filters, to "tune" the "white" light (or approximately white light) illumination signal to a range of wavelengths that are designed to not interfere with the detection of emitted light 112 that originates solely through fluorescence effect or other intrinsic property of nervous tissue 105 in a tissue region of interest 104. According to various embodiments of the system 100, all or a portion of reflected light 114 (mostly resulting from illumination light emitted by the illumination light source 103), emitted light 112, and non-emitted ambient light, if any, will be collected by a receiving optical train 117 of interrogation unit 120.

In some alternative embodiments, excitation light source 102 (see FIG. 4) resides in a location remote from interrogation unit 120, and excitation light 110 is transmitted to interrogation unit 120 through a light transmission means, such as fiber-optic bundle, for example. A remote excitation light source 102 may be a "free-standing" device, or may be housed within or coupled to a console such as those used in robotically assisted or computer-assisted surgery, a medical device cart, or the like. The light transmission means may be unitary with first cable 126 or may be mechanically and optically coupled between excitation light source 102 and interrogation unit 120 as a separate elongate cable-like structure, for example.

Excitation light source 102 generates excitation light that can comprise a broad band of electromagnetic radiated signal wavelengths, or alternatively excitation light confined to a narrower electromagnetic radiated signal wavelength range. For example, in some embodiments, excitation light source 102 can comprise a narrow-wavelength range source such as a light-emitting diode (LED) or a laser. In some embodiments, excitation light source 102 comprises a wide electromagnetic radiated signal wavelength-range "white" light (or approximately white light) source, such as a halogen (xenon) lamp, a 450-Watt xenon lamp, a tungsten-halogen lamp, a mercury arc lamp, or the like, for example.

Excitation light source 102 emits excitation light 110 (electromagnetic radiated signal) which passes from source optical train 116 of interrogation unit 120 to illuminate (radiate) a tissue region of interest 104. Excitation light source 102 is configured to emit excitation light 110 at a particular wavelength to stimulate or excite nervous tissue in the tissue region of interest 104 through an effect intrinsic to the nervous tissue; for example, an endogenous autofluorescence effect. Because the effect is intrinsic i.e., of the essential nature or constitution of the tissue and originating wholly from within the nervous tissue, fluorescent (or other) dyes, fluorescent markers, fluorescent tissue probes, and the like, are not necessary and are not used for operation of tissue imaging system 100.

The generated wavelength of excitation light 110 by excitation light source 102, which might be also optically coupled through an optical filter, maximizes the difference between intrinsic endogenous fluorescence effects of the healthy nervous tissue and the surrounding healthy non-nervous tissue, in some embodiments. In a visual image display, for example, a remarkable difference in images can be seen on a display screen between a highlighted image corresponding to endogenous fluorescence effects of nervous tissue (see, for example, 802 in FIG. 8) in a tissue region of interest and a not highlighted and darker image (see, for example, 804 in FIG. 8) corresponding to a lack (or minimal presence) of fluorescence effects and reduced reflected light from adjacent and/or surrounding non-nervous tissue in the tissue region of interest. The very remarkable difference between the two images on the display screen, e.g., the highlighted image corresponding to endogenous autofluorescence effects of nervous tissue visually contrasted from the not highlighted and darker image corresponding to a lack (or minimal presence) of fluorescence effects and reduced reflected light from adjacent and/or surrounding non-nervous tissue, enhances visualization of a nervous tissue in contrast to non-nervous tissue adjacent to or surrounding the nervous tissue in a tissue region of interest (under examination). This contrasted visualization of nervous tissue and non-nervous tissue in a tissue region of interest can provide significant information assisting, for example, a surgeon to perform surgical procedures on a patient.

Figure 19:
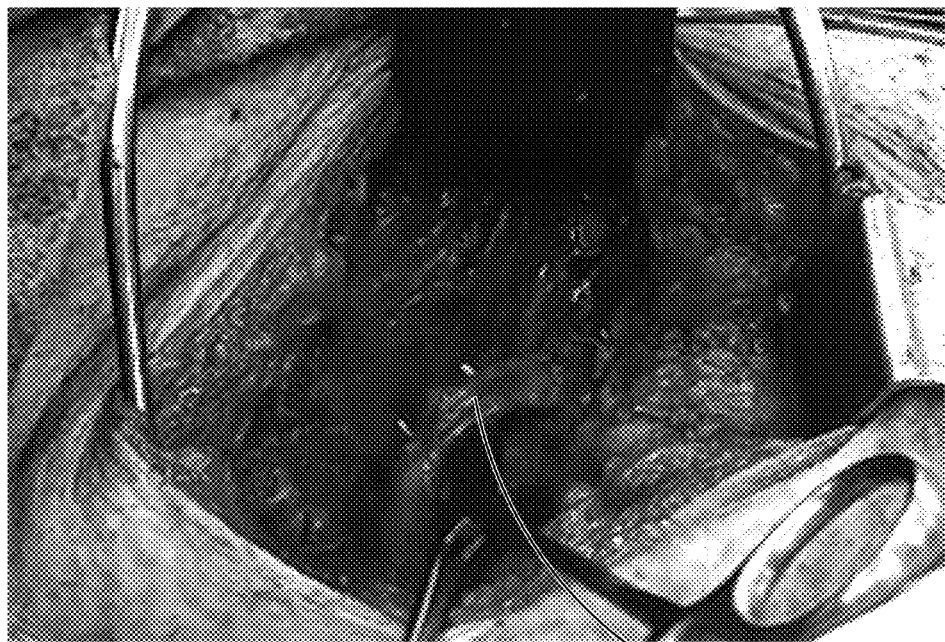
FIGS. 19 and 20 illustrate a first example set of images corresponding to a surgical field, showing the surgical field viewed under ambient light illumination, and alternatively showing the surgical field viewed with a tissue imaging system according to various embodiments of the invention.
Figure 20:
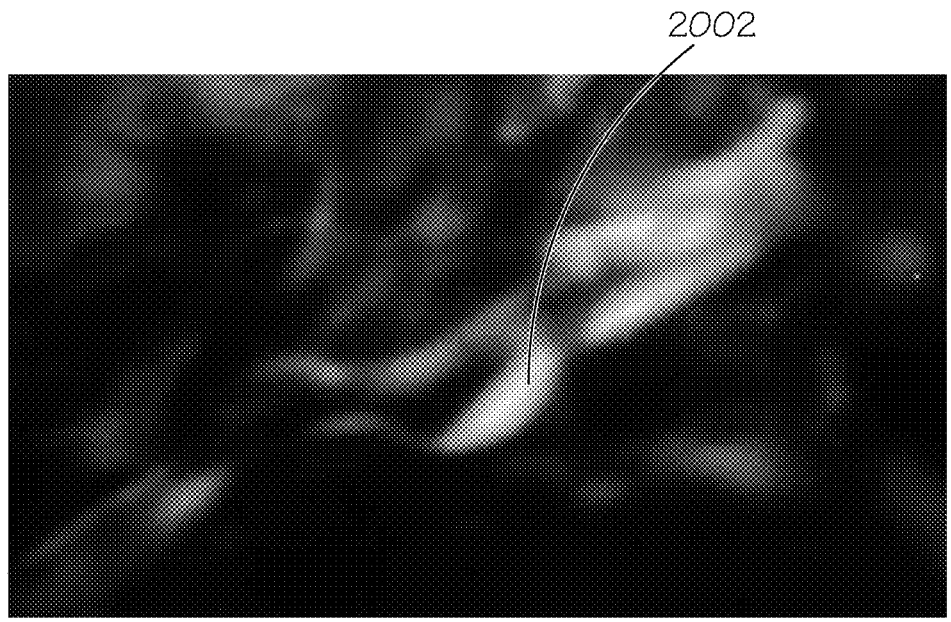

Several stark examples of this contrast are illustrated below, according to various embodiments. As a first example, compare the surgical visual field image in FIG. 19 to the corresponding surgical visual field image shown in FIG. 20. In FIG. 19, under ambient white light conditions, it is very difficult to distinguish the presence of nervous tissue 1902 against non-nervous tissue that is adjacent to and/or surrounding the nervous tissue 1902. In FIG. 20, using an example embodiment of a Dendrite-camera 1600 based tissue imaging system 100, the formed highlighted image of nervous tissue 2002 is clearly observable contrasted against the darker background image of the non-nervous tissue that is adjacent to and/or surrounding the nervous tissue 2002.

Figure 22B:
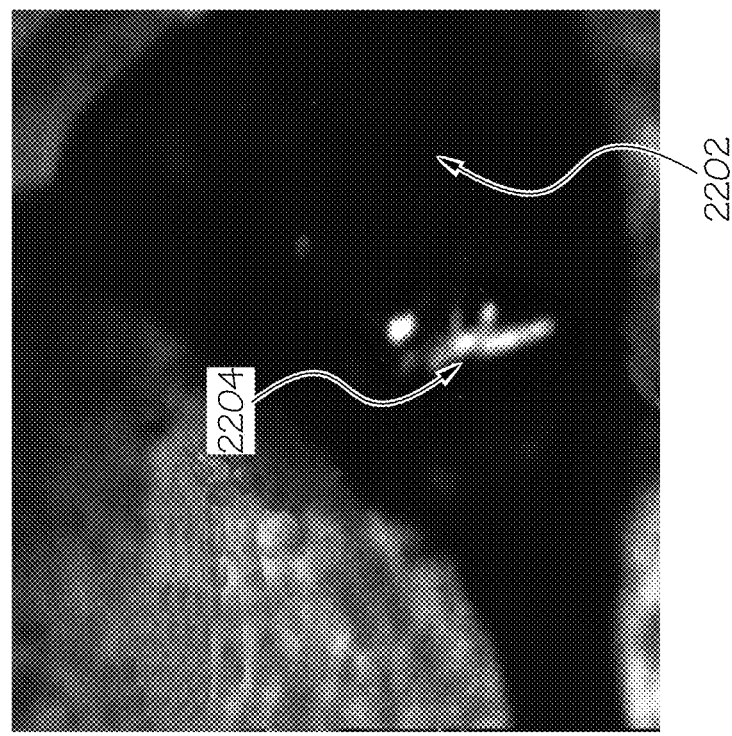
FIGS. 22A and 22B illustrate a second example set of images corresponding to a surgical field, showing the surgical field viewed under ambient light illumination, and alternatively showing the surgical field viewed with a tissue imaging system according to various embodiments of the invention.
Figure 22A:
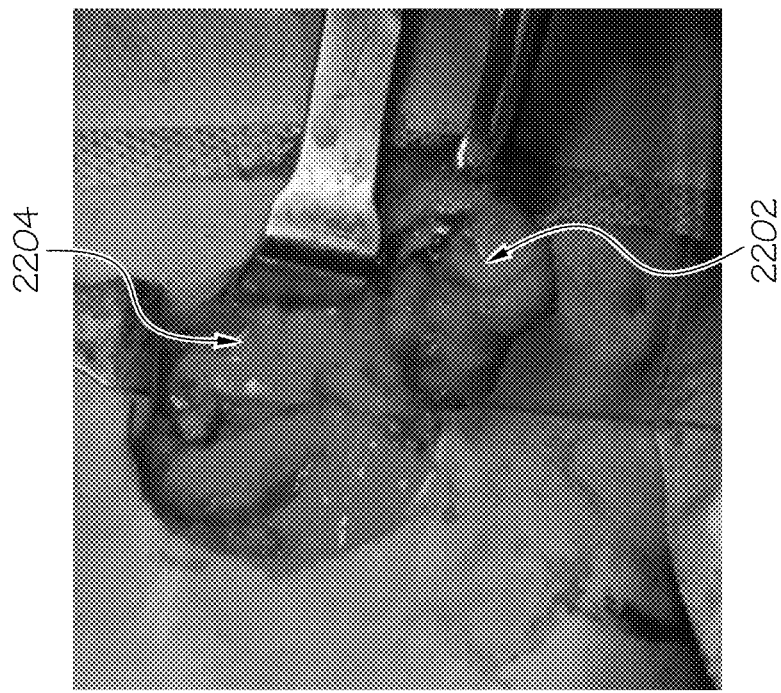

As a second example, compare the surgical visual field image in FIG. 22A to the corresponding surgical visual field image shown in FIG. 22B. FIGS. 22A and 22B illustrate comparative images of a submaxilectomy procedure in which the hypoglossal nerve must be identified and spared. In FIG. 22A, under ambient white light conditions, it is very difficult to distinguish the presence of nervous tissue 2204 against non-nervous tissue 2202 that is adjacent to and/or surrounding the nervous tissue 2204. In FIG. 22B, using an example embodiment of a Dendrite-camera 1600 based tissue imaging system 100, the formed highlighted image of nervous tissue 2204 is clearly observable contrasted against the darker background image of the non-nervous tissue 2202 that is adjacent to and/or surrounding the nervous tissue 2002. FIG. 22A shows the submandibular gland but it does not clearly show the hypoglosal nerve boundaries. In contrast, FIG. 22B shows that when the Dendrite-camera 1600 based system 100 is activated, the nerve 2204 can be clearly observed (contrasted to non-nervous tissue 2202 that is adjacent to and/or surrounding the nervous tissue 2204) thanks to the autofluorescence emitted by the nervous tissue 2204 in the surgical visual field image shown in FIG. 22B and captured by the example Dendrite camera device 1600.

Figure 23B:
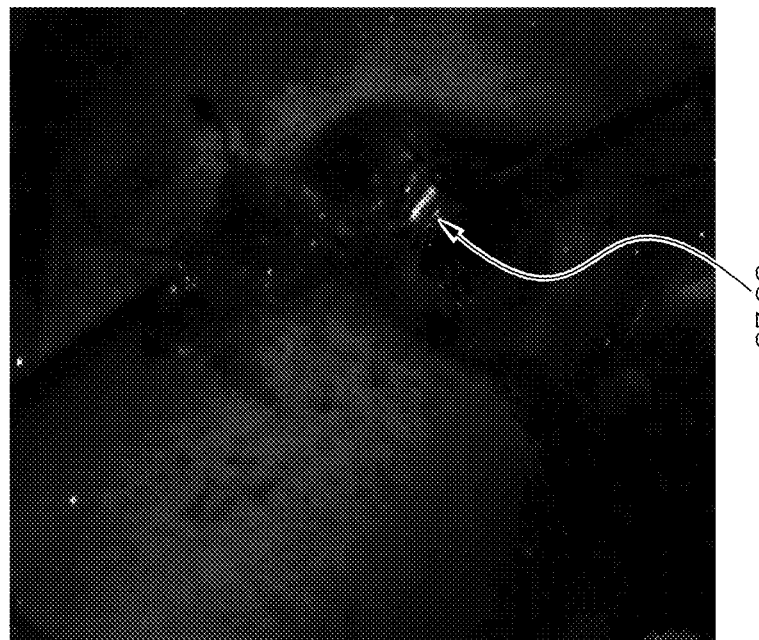
FIGS. 23A and 23B illustrate a third example set of images corresponding to a surgical field, showing the surgical field viewed under ambient light illumination, and alternatively showing the surgical field viewed with a tissue imaging system according to various embodiments of the invention.
Figure 23A:
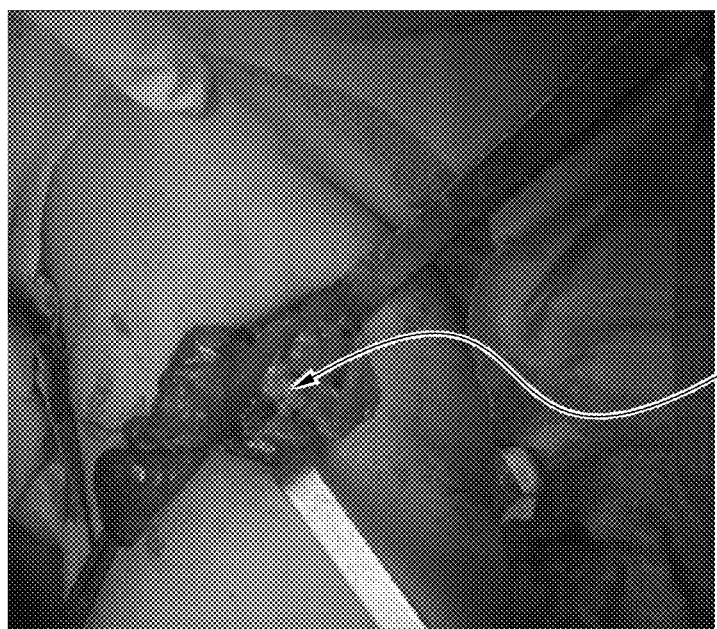

As a third example, compare the surgical visual field image in FIG. 23A to the corresponding surgical visual field image shown in FIG. 23B. FIGS. 23A and 23B illustrate comparative images of a thyroidectomy procedure in which the laryngeal nerve must be identified and spared. FIG. 23A shows the retracted thyroid gland. Under ambient white light conditions, it is very difficult to distinguish the presence of laryngeal nerve 2302 against non-nervous tissue that is adjacent to and/or surrounding the nervous tissue 2302. In FIG. 23B, using an example embodiment of a Dendrite-camera 1600 based tissue imaging system 100, the formed highlighted image of the nervous tissue 2302 is clearly observable contrasted against the darker background image of the non-nervous tissue that is adjacent to and/or surrounding the nervous tissue 2302, thanks to the autofluorescence emitted by the nervous tissue 2302 in the surgical visual field image shown in FIG. 23B which is captured by the example Dendrite camera device 1600.

Figure 24A:
FIGS. 24A and 24B illustrate a fourth example set of images corresponding to a surgical field, showing the surgical field viewed under ambient light illumination, and alternatively showing the surgical field viewed with a tissue imaging system according to various embodiments of the invention.
Figure 24B:

As a fourth example, compare the surgical visual field image in FIG. 24A to the corresponding surgical visual field image shown in FIG. 24B. FIGS. 24A and 24B illustrate comparative images of a fully dissected neck of a patient. In FIG. 24A, under ambient white light conditions, it is very difficult to distinguish the presence of nervous tissue (e.g., nerve fascicles) 2402, 2404, against non-nervous tissue that is adjacent to and/or surrounding the nervous tissue 2402, 2404. In FIG. 24B, using an example embodiment of a Dendrite-camera 1600 based tissue imaging system 100, the formed highlighted image of nervous tissue 2402, 2404, is clearly observable contrasted against the darker background image of the non-nervous tissue that is adjacent to and/or surrounding the nervous tissue 2402, 2404, thanks to the autofluorescence emitted by the nervous tissue 2402, 2404, in the surgical visual field image shown in FIG. 24B and captured by the example Dendrite camera device 1600.

In some example embodiments, the wavelength of excitation light 110 is a range between about 365 nanometers (nm) and about 400 nm. In some example embodiments, the wavelength of excitation light 110 is a range of wavelengths between about 382 nm and about 392 nm. In some example embodiments, the wavelength of excitation light 110 can be a range of wavelengths between about 455 nm and about 510 nm. In some example embodiments, the wavelength of excitation light 110 can be about 485 nm.

Source optical train 116 directs excitation light 110 from interrogation unit 120; i.e., to illuminate a tissue region of interest. Source optical train 116 may be proximate to or contiguous with excitation light source 102. In some embodiments, source optical train 116 comprises an optical lens, or a plurality of optical lenses to appropriately focus or disperse and direct excitation light 110 for illumination of tissue region of interest 104. In some embodiments, excitation light source 102 illuminates tissue region of interest 104 directly with excitation light 110 and interrogation unit 120 does not comprise source optical train 116. In some embodiments, source optical train 116 is contained within excitation light source 102 separate from interrogation unit 120. In some embodiments, source optical train 116 comprises a fiber-optic bundle as discussed herein. According to the embodiment, source optical train 116 may comprise any combination including one or more of an optical lens, a plurality of optical lenses, or a fiber-optic bundle, without limitation.

In some embodiments, source optical train 116 comprises an excitation filter configured to narrow, constrict, band-pass, or "tune" the wavelength of excitation light 110 to a range optimal for causing the healthy nervous tissue, by endogenous autofluorescence effect, to produce emitted light (fluorescence light) 112, which may be in a narrow, constricted, band-pass, range of wavelengths, while causing minimal or no fluorescence of the surrounding healthy non-nervous tissue. In particular, any minimal fluorescence of the surrounding healthy non-nervous tissue would emit other light outside of the narrow, constricted, band-pass, range of wavelengths of the emitted light 112 from the nervous tissue. In some embodiments, by use of one or more optical filters optically coupled to a source optical train and one or more illumination light sources, any illumination light (such as from the illumination light source 103 shown in FIG. 4) and accordingly any reflected light from the tissue region of interest 104 may be rejected from or significantly reduced in the narrow, constricted, band-pass, range of wavelengths of the emitted light 112 from the nervous tissue. Also, by use of one or more optical filters optically coupled to a receiving optical train and to a light detection device (e.g., imaging camera device), any excitation light 110 would be rejected from or significantly reduced in the narrow, constricted, band-pass, range of wavelengths of the emitted light 112 from the nervous tissue, while allowing to pass, in certain embodiments, illumination light reflected from the tissue region of interest. Additionally, any minimal fluorescence effects of the non-nervous tissue (from radiated illumination light, if any, and from the radiated excitation light) would likely emit light that is substantially outside of, and would be rejected from or significantly reduced in the narrow, constricted, band-pass, range of wavelengths of the emitted light 112 from the nervous tissue. The addition of the one or more filters, whether coupled to the source optical train or coupled to the receiving optical train, as discussed above, may enhance the contrast of the emitted light 112 from the nervous tissue compared to any light from the non-nervous tissue in the tissue region of interest.

Excitation filter (e.g., see Filter 2 in FIG. 12 and filter 1306 in FIG. 13) is particularly useful for embodiments wherein excitation light source 102 is a broad-band white light source, such as a halogen or mercury-arc source. In the current example, excitation light 110 is radiated from a more narrow-band source, such as certain LED or laser excitation light sources. Accordingly, in some embodiments, an excitation filter is a bandpass filter. In some embodiments, an excitation filter can be a low-pass (long pass) filter. In some embodiments, an excitation filter is a high-pass (short pass) filter. In some embodiments, an excitation filter is an about 382 nm to an about 392 nm bandpass filter. In some embodiments, an excitation filter comprises an about 300 nm high-pass (short pass) filter. In some embodiments, an excitation filter comprises an about 400 nm low-pass (long pass) filter. In some embodiments, an excitation filter is an about 300 to an about 400 nm bandpass filter. In some embodiments, an excitation filter is an about 320 to an about 380 nm bandpass filter. In some embodiments, an excitation filter is an about 325 nm to an about 375 nm bandpass filter. In some embodiments, an excitation filter comprises an about 350 nm low-pass (long pass) filter. In some embodiments, an excitation filter comprises an about 300 nm low-pass (long pass) filter. In some embodiments, an excitation filter comprises an about 400 nm high-pass (short pass) filter.

Figure 15:
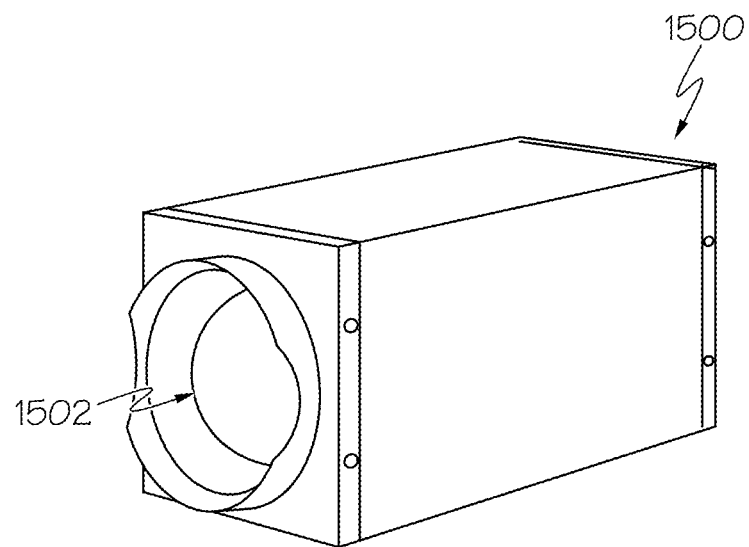
FIGS. 15 and 16 are two illustrations of camera components suitable for use in various embodiments of a tissue imaging system.
Figure 16:
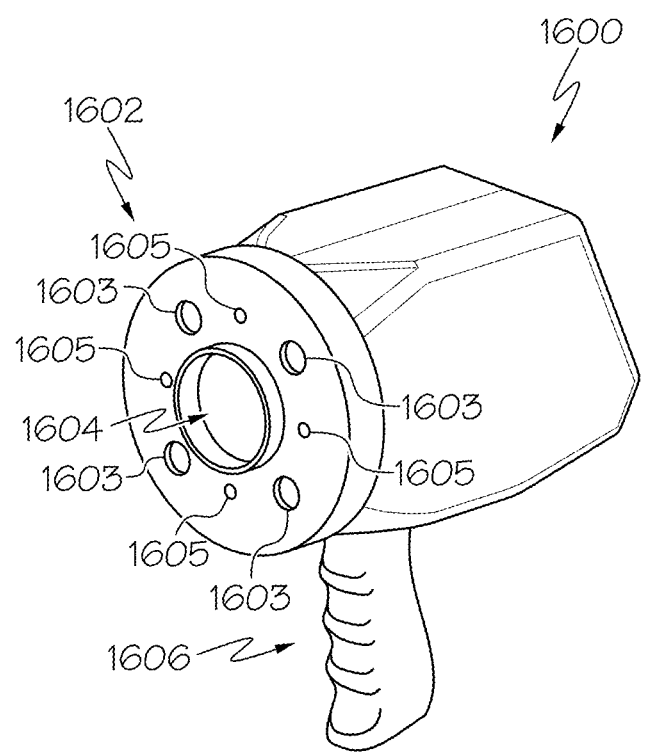
Figure 21:
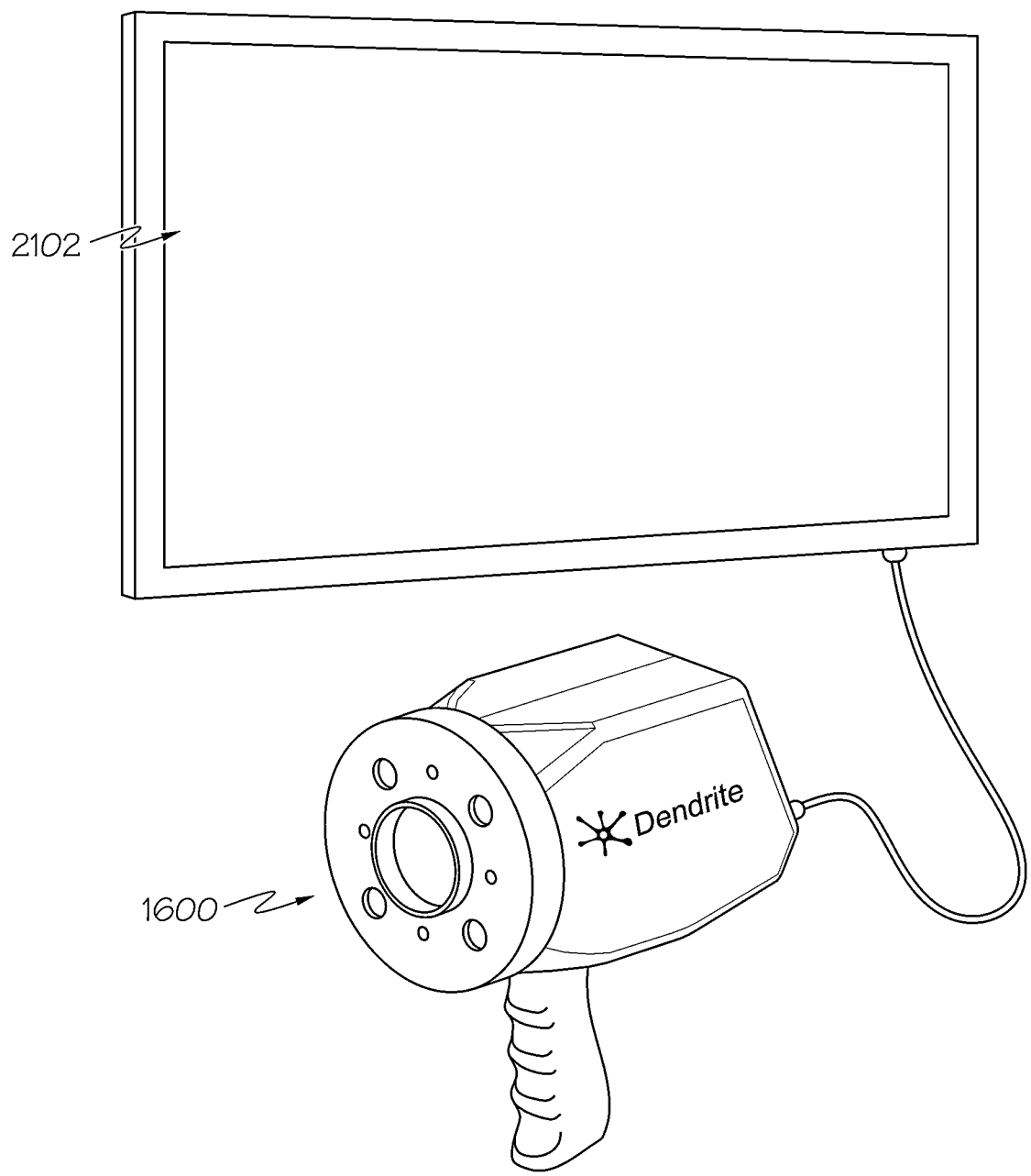
FIG. 21 is an illustration of an example Dendrite camera device based tissue imaging system, according to various embodiments.

It should be noted that FIGS. 15 and 16 illustrate various example embodiments of a camera imaging device, which may be also referred to as a Dendrite camera device. A camera 1500, as shown in FIG. 15 includes a camera housing and a receiving optical train including a lens 1502 and possibly, in certain embodiments, may also include with the lens, or in proximity with the lens, one or more optical filters 1502. FIG. 16 illustrates an example of a tissue imaging device 1600, which may also be referred to as a Dendrite camera. The tissue imaging device 1600 can be hand-held by its handle 1606. The tissue imaging device 1600, in this example, includes a ring portion 1602 that includes a plurality of light sources 1603 and possibly one or more sensor/detector/camera units 1605. A lens/filter 1604 (e.g., components of a receiving optical train) is located in a central region of the ring portion 1602. The ring portion 1602 includes components 1603 of a source optical train that couples one or more exciting light signals and/or one or more illumination light signals, from one or more light sources in the tissue imaging device 1600. Light signals from a tissue region of interest are received and directed through the lens/filter 1604 (e.g., components of a receiving optical train) to a camera device in the tissue imaging device 1600. FIG. 21 illustrates an example tissue imaging system including the Dendrite camera device 1600 communicatively coupled via with a computer processing system and a touch panel display device 2102. In this example, the computer processing system and the touch panel display device 2102 are integrated in a housing configured for use in a sterile environment.

Figure 17:
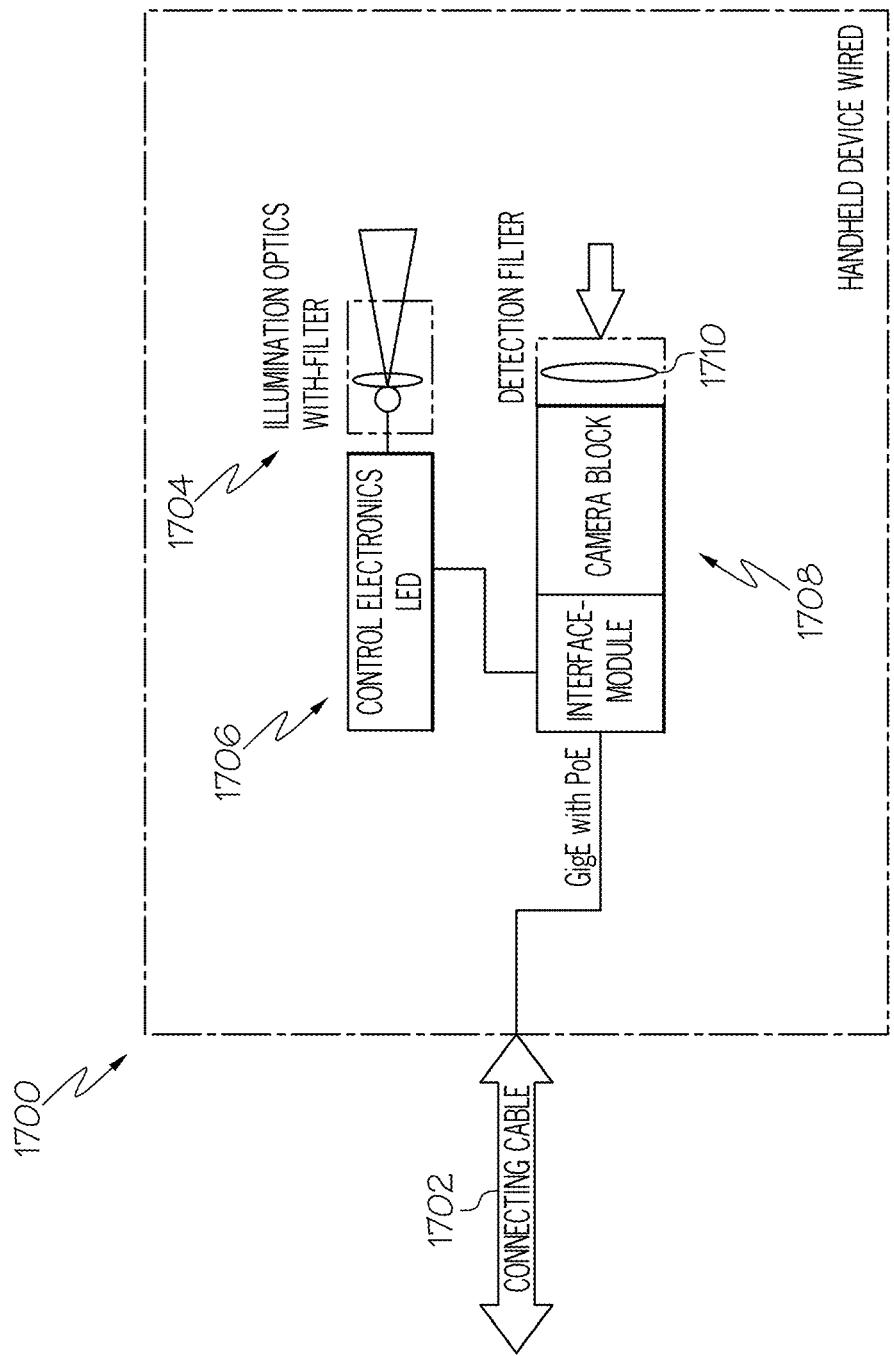
FIGS. 17 and 18 are block diagrams illustrating example components of a tissue imaging system, according to various embodiments.
Figure 18:
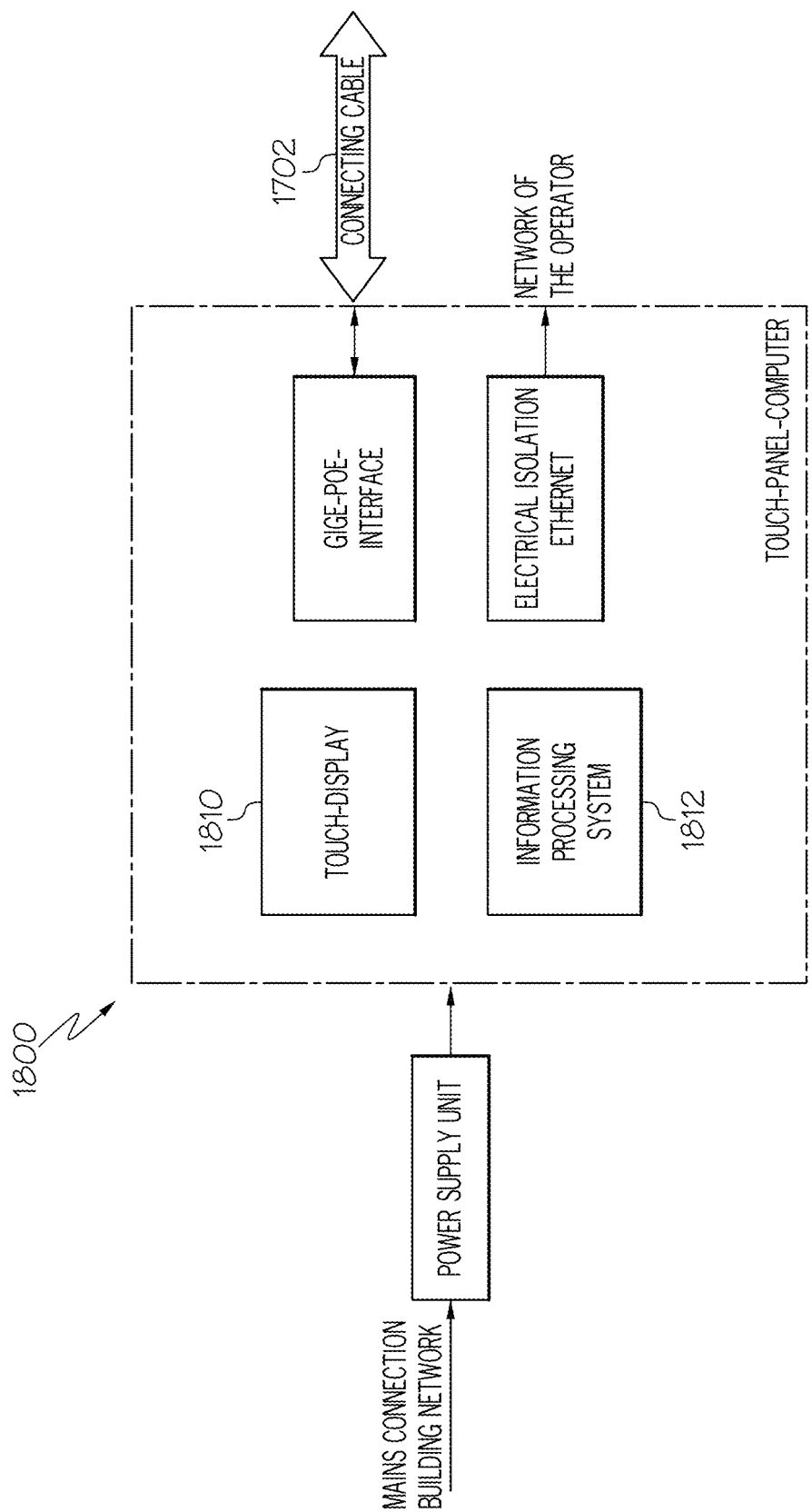

FIGS. 17 and 18 illustrate example components of a tissue imaging system, according to various embodiments. An example camera imaging device 1700, which may also be referred to as a Dendrite camera device, is shown in FIG. 17. This example camera imaging device 1700 can be handheld by a user. The device 1700 can be connected via an Ethernet network link 1702 to a computer processing system 1800 shown in FIG. 18. The camera imaging device 1700 includes various components such as illumination optics including at least one light source 1706 with controlling electronics. A source optical train 1704 is also shown coupling light signals from the at least one light source 1706 through one or more lenses and filters. A camera block 1708 includes a computer interface that connects the camera electronic input-output signals through the Ethernet connecting cable to the computer processing system 1800. The camera 1708 also comprises a receiving optical train that includes one or more detection filters and/or lenses 1710. The computer processing system 1800 includes an information processing system 1812, which may include one or more processors, memory, storage memory, power circuitry, and data communication interfaces. A touch panel display device 1810 is shown as a component of the computer processing system 1800. This touch panel device 1810 provides output user interface devices and input user interface devices to communicate with a user of the computer processing system 1800. The computer processing system 1800 also includes a computing networking interface that can be communicatively coupled with an external network, which can be used to communicate information and control signals between the computer processing system 1800 and another computing device communicatively coupled with the network.

Continuing with the discussion of the example tissue imaging system 100, and with particular reference to FIG. 3, the tissue region of interest 104 in response to being illuminated with excitation light 110 directs light back to the interrogation unit 120. This directed light includes a reflected light 114, including possibly a reflected component of excitation light 110 from the tissue region of interest. The heathy nervous tissue in the tissue region of interest 104, which has intrinsic fluorescent properties when illuminated with excitation light 110, produces an emitted light 112. Emitted light 112 originates solely through fluorescence or other intrinsic property of a portion (e.g., the healthy nervous tissue) of the tissue region of interest 104. All or a portion of reflected light 114, emitted light 112, and non-emitted ambient light or other illumination light from an illumination light source 103, will be collected by receiving optical train 117 of interrogation unit 120, in some embodiments of the system 100.

Figure 11:
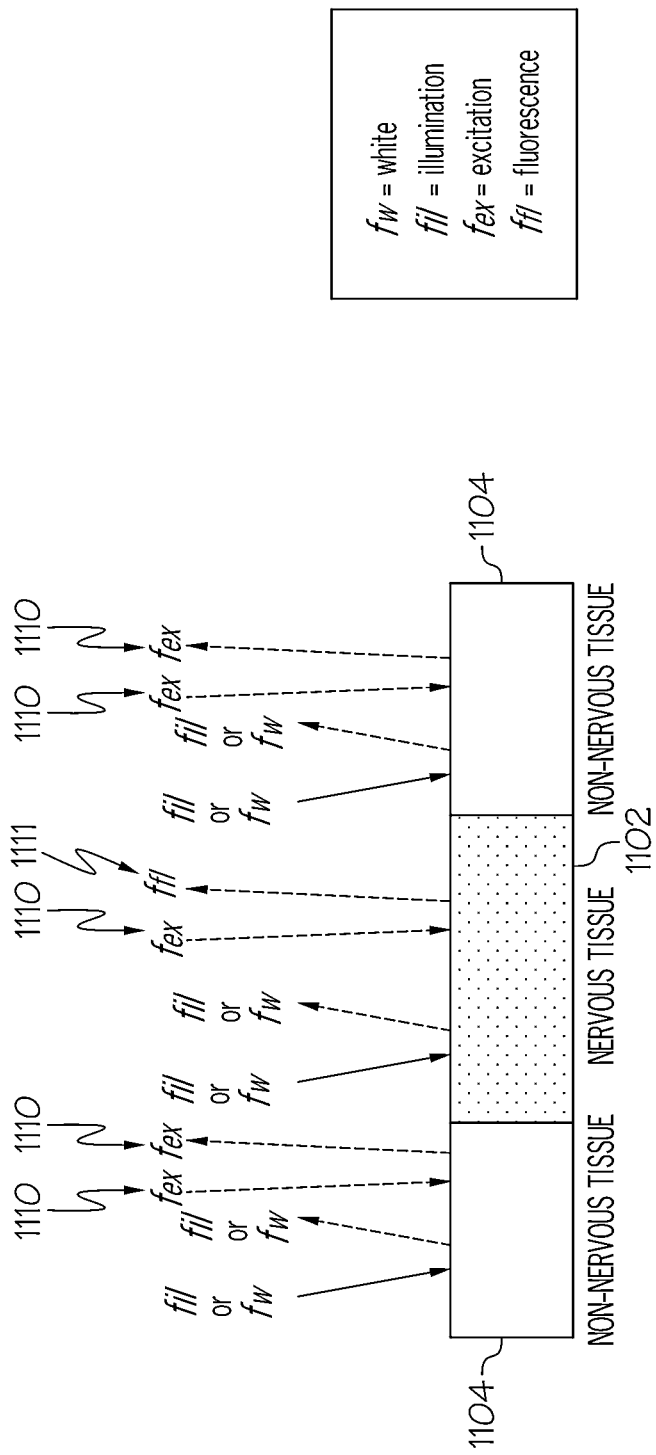
FIG. 11 is an illustration of an example tissue region of interest including nervous tissue and non-nervous tissue, and showing example different wavelength electromagnetic signals including signals radiated onto the tissue region of interest and signals reflected from the tissue region of interest, and showing an excitation signal radiated onto nervous tissue in the tissue region of interest and endogenous autofluorescence signal emitted from the nervous tissue in response to the excitation signal radiated onto the nervous tissue.

FIG. 11 illustrates an example of various types of lights that may be illuminated onto a tissue region of interest comprising nervous tissue 1102 and non-nervous tissue 1104 adjacent to or surrounding the nervous tissue 1102. Excitation light 1110 is emitted from a light source, such as in a tissue imaging system 100. The excitation light 1110 is design in a system to particularly induce or elicit an endogenous autofluorescence effect of the nervous tissue 1102. This may effect may be due to biological and/or chemical causes in the nervous tissue, such as due to its composition and other intrinsic properties of the nervous tissue.

Nervous tissue, for example, can be characterized by high lipid and protein content. It does not contain large amounts of saccharides. Complex lipids (e.g. phospholipids and sphingophospholipids) and unesterified cholesterol can be the most abundant lipids. Proteins, including protein crystals, can autofluoresce when excited with certain wavelength of ultraviolet (UV) light. Intrinsic properties of nervous tissue that can autofluoresce when excited by certain wavelengths of UV light may be significantly different from other non-nervous tissue in a patient's body. The inventors have observed that under certain lighting conditions a tissue region of interest that contains healthy nervous tissue and healthy non-nervous tissue can emit a high luminance of endogenous autofluorescence light 1111 from the nervous tissue 1102 in response to illumination of the nervous tissue 1102 with excitation light of a certain range of wavelengths. One such range of wavelengths of excitation light appears to be in a range of about 382 nm to about 392 nm. The nervous tissue appears to endogenously autofluoresce, in response to being illuminated by the excitation light 1110 comprising the above described range of wavelengths. The endogenous autofluorescence light 1111 wavelengths which appear highest in luminance are in a range of about 433 nm and about 450 nm. The excitation light 1110 that illuminates the non-nervous tissue 1104 will be reflected from the non-nervous tissue 1104 as reflected light at the same wavelength range (about 382 nm to about 392 nm) as the excitation light 1110. Any illumination light on the tissue region of interest, which could include wavelengths in a wider range 1008 (see FIG. 10) or in a narrower range 1010, will mostly be reflected from the tissue region of interest including both from the healthy nervous tissue 1102 and from the healthy non-nervous tissue 1104. In certain embodiments that use illumination light in the wider range of wavelengths (approximately white light) 1008, to improve detection of the endogenous autofluorescence light 1111, one or more optical filters (including a notch filter) can couple illumination light from a light source into a source optical train while also substantially filtering out the range of wavelengths 1006 that are characteristic of the endogenous autofluorescence light 1111 emitted from the nervous tissue 1102. This "notch" filtering of the illumination light can reduce possible interference from reflected illumination light while detecting the wavelengths of the endogenous autofluorescence light 1111.

Figure 4:
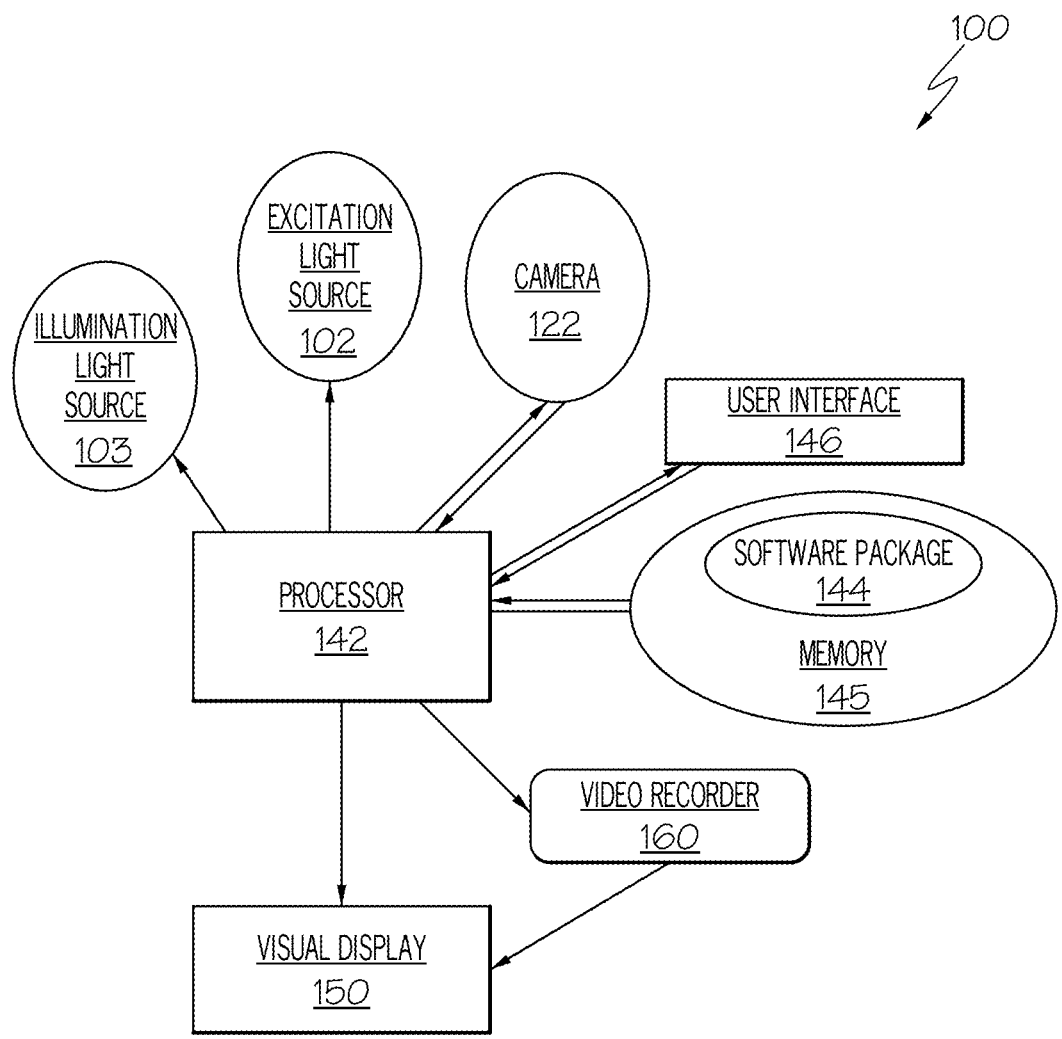
FIG. 4 is a block diagram illustrating an example of a tissue imaging system, according to various embodiments.

Receiving optical train 117, according to various embodiments, comprises an optical lens or a plurality of optical lenses, and is configured to focus and direct light comprising emitted light 112 onto a camera 122 (see FIG. 4). In some embodiments, receiving optical train 117 comprises a single focusing lens. In some embodiments, receiving optical train 117 comprises a plurality of (any number, combination, and arrangement of) focusing lenses and possibly dispersing lenses configured to focus at least emitted light 112 onto the camera 122. Some embodiments of system 100 do not comprise receiving optical train 117, wherein camera 122 is a "chip on a stick" image-sensor charge coupled device ("CCD") camera. Some embodiments of receiving optical train 117 can comprise a detection filter but do not comprise a lens.

In some embodiments, receiving optical train 117, as shown in FIG. 3, comprises a detection filter. In some embodiments, a detection filter is an optical filter that filters out reflected light 114 and ambient light having wavelengths outside of the range of the detection filter. In some embodiments, however, receiving optical train 117 does not comprise a detection filter. The detection filter may allow only desired wavelengths of light (e.g., wavelengths that correspond to the nervous tissue emitted light—in response to an endogenous autofluorescence effect induced or elicited by illumination by the excitation light) to pass through the detection filter to a camera 122 (see FIG. 4). In some embodiments of system 100, the light-filtering function of a detection filter is performed digitally by an image processing software package residing on a data processor or information processing system.

The appropriate detection filter can depend on other aspects of the system 100, particularly with respect to the wavelength of emitted light 112 which, in turn, depends on the intrinsic properties of the nervous tissue, such as spinal dura or duramadre, targeted for visualization. In addition to configuring a detection filter to allow passage of wavelengths corresponding to emitted light 112, such as nervous tissue emitted light, detection filter 124 may also be configured to allow wavelengths of emitted light 112 to pass that enable visualization of non-nervous tissue adjacent to or surrounding a peripheral nerve, wherein the adjacent or surrounding non-nervous tissue emits light at a particular wavelength or in a particular wavelength range that is different from the wavelength(s) of the excitation light and different from the emitted light 112 such as nervous tissue emitted light. Nervous tissue intrinsically form emitted light 112 of a higher intensity than many non-nervous tissues in response to the same intensity (luminosity) and wavelength of excitation light 110. For this reason, light emitted from non-nervous tissue adjacent to or surrounding a nervous tissue, such as adipose or muscle tissue, will have a significantly lower intensity than light emitted from the nervous tissue. The surrounding non-nervous tissue can still be visualized, but the nervous tissue can be readily visually distinguished from the surrounding non-nervous tissue, such as illustrated in FIG. 8 and in FIG. 20.

In some embodiments, a detection filter is a bandpass filter that preferentially allows fluorescence light 1006 (see FIG. 10) to pass comprising wavelengths in a range of about 433 nm to about 450 nm consistent with a range of excitation light 1004 in a range of wavelengths of about 382 nm to about 392 nm. In some embodiments, detection filter is a bandpass filter with a range of about 450 nm to about 575 nm. In some embodiments, detection filter 124 is a bandpass filter with a range of about 480 nm to a range of about 500 nm. In some embodiments, detection filter is a bandpass filter with a range of about 450 nm to about 575 nm. In some embodiments, detection filter is a bandpass filter with a range of about 425 nm to about 525 nm. In some embodiments, detection filter is a bandpass filter with a range of about 440 nm to about 570 nm.

In some embodiments, detection filter is a low-pass (long pass) filter with a range of longer than about 400 nm. In some embodiments, detection filter comprise a low-pass (long pass) filter with a range of longer than about 425 nm. In some embodiments, detection filter is a low-pass (long pass) filter with a range of longer than about 450 nm.

In some embodiments, detection filter comprises a high-pass (short pass) filter with a range of wavelengths shorter than about 600 nm. In some embodiments, detection filter comprises a high-pass (short pass) filter with a range of wavelengths shorter than about 575 nm. In some embodiments, detection filter comprises a high-pass (short pass) filter with a range of wavelengths shorter than about 550 nm. In some embodiments, detection filter comprises a high-pass (short pass) filter with a range of wavelengths shorter than about 510 nm.

Camera 122 receives light from receiving optical train 117, in some embodiments.

In some embodiments, camera 122 is configured to communicate digital information representing light collected from receiving optical train 117 to a processor, wherein the processor digitally processes the information to generate a visual image displayed on a digital screen or monitor. Camera 122, in some embodiments, is an image sensor/detector. Accordingly, in some embodiments, camera 122 is a digital camera module configured to couple to a processor. Camera 122 is a monochromatic or polychromatic digital camera, in some embodiments. One non-limiting example of a suitable camera 122 is the VM-010-KSP09.A0 digital camera module (PHYTEC Messtechnik GmbH, Mainz, Germany). In some embodiments, camera 122 is an optical camera having an eyepiece for direct visualization of a non-digital visual image. Camera 122, with or without receiving optical train 117, can be optically coupled to visualization devices other than interrogation unit 120, such as an operating microscope/laparoscope, thoracoscope, arthroscope, bronchoscope, ureteroscope, or the like; for a flexible fiber-optic endoscope, in some embodiments.

Figure 12:
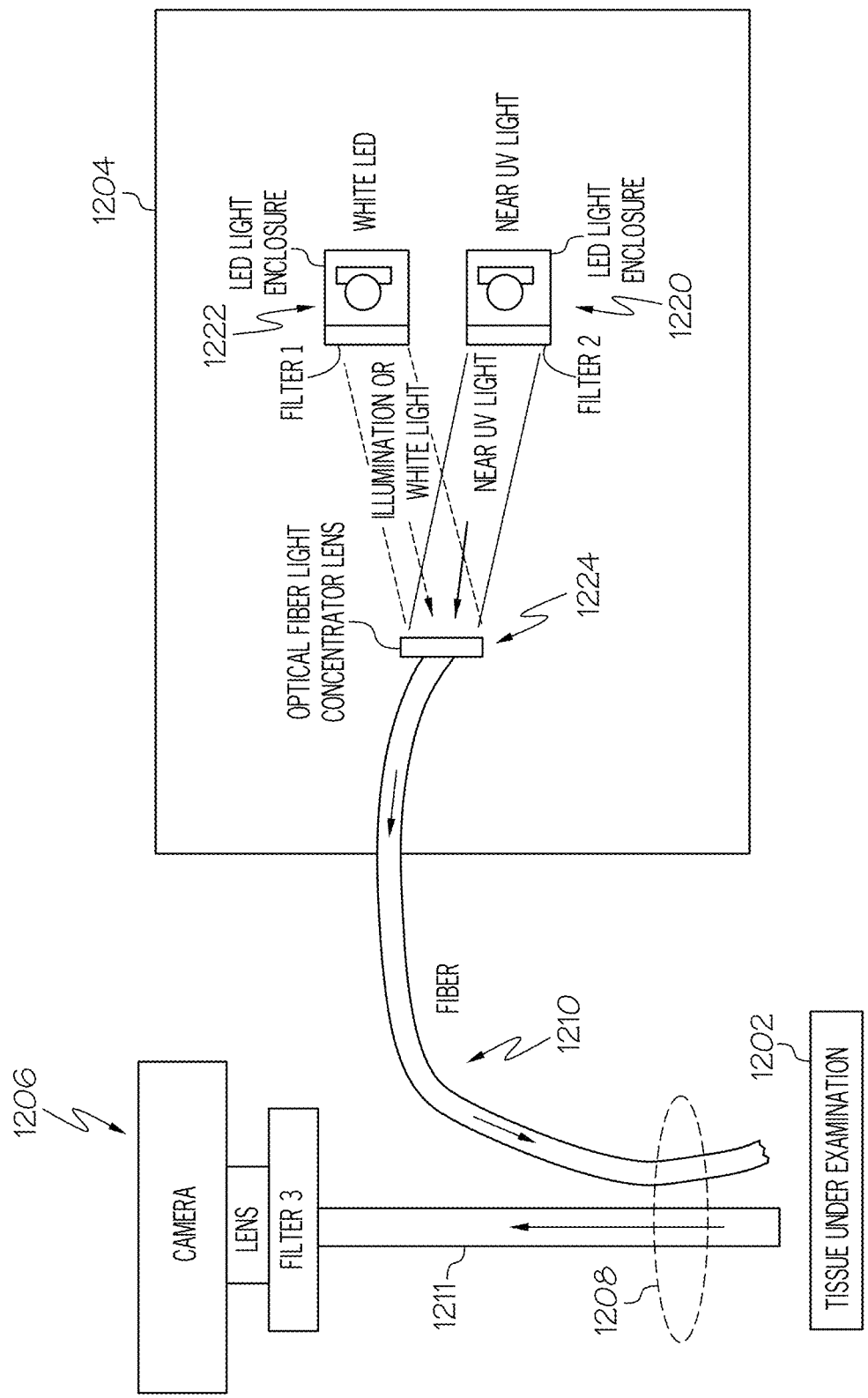
FIG. 12 is an illustration of several components of a first example tissue imaging system, according to various embodiments.

One non-limiting example of a camera 1206 optically coupled to a visualization device such as a flexible endoscope 1208 is illustrated in FIG. 12, according to various embodiments. A tissue imaging system can be used to examine a tissue region of interest (tissue under examination) 1202 inside a substantially enclosed cavity of a patient's body. A light box unit 1204, according to this example, optically couples selectable light signal from one or more light sources 1220, 1222, to an optical light concentrator 1224, which couples light emitted from the selected one or more light sources 1220, 1222, through a fiber-optic cable (fiber-optic light guide) 1210 which guides the emitted light to, for example, a rigid or flexible endoscope device 1208. The rigid or flexible endoscope device 1208 includes a further light guide that guides the emitted light into, for example, the substantially enclosed cavity of a patient's body to thereby illuminate a tissue region of interest 1202 with the excitation light. The tissue region of interest 1202 may include nervous tissue adjacent to or surrounded by non-nervous tissue. The nervous tissue and the non-nervous tissue may respectively comprise healthy nervous tissue and healthy non-nervous tissue.

Figure 10:
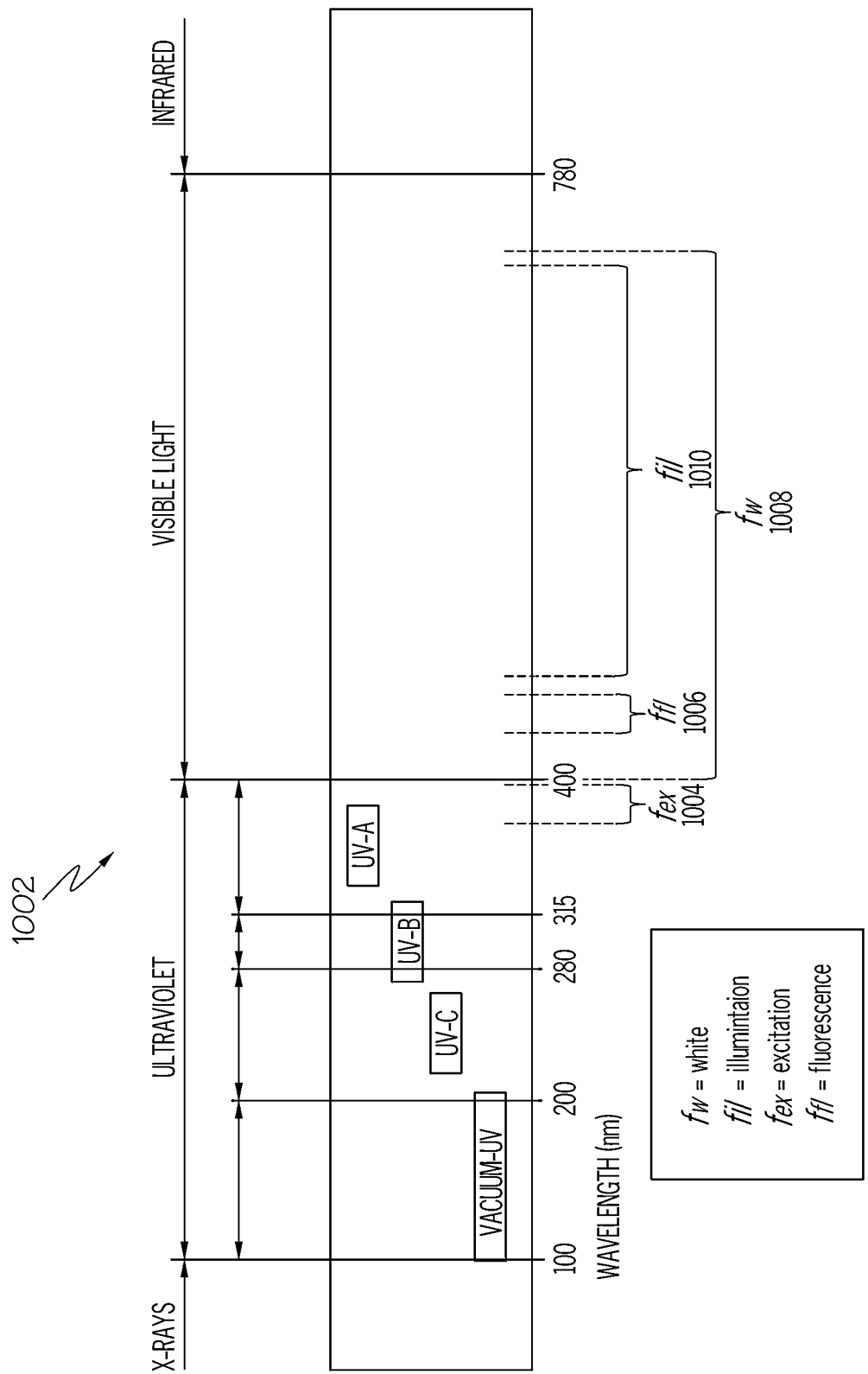
FIG. 10 is a diagram of an electromagnetic spectrum including UV spectrum, Visible Light spectrum, and IR spectrum, illustrating several wavelength bands of interest according to various embodiments.

According to the example, the excitation light (e.g., such as in a near UV light range of wavelengths between about 382 nm and about 392 nm that can be "tuned" by selection of a band-pass optical filter—filter 1—in a first light source 1220) can be selectively emitted from the first light source 1220 in the one or more light sources 1220, 1222, under control of a processor, responsive to computer instructions, operating in an information processing system 1812 (see FIG. 18). According to the example, FIG. 10 illustrates in an electromagnetic spectrum 1002 the range of wavelengths for the excitation light 1004. Each of the optical filters—filter 1, filter 2, and filter 3, shown in FIG. 12, can include one or more optical filters that can be used to "tune" a design of a wavelength range for light signal. Source light filters—filter 1 and filter 2—"tune" light signal emitted from each light source 1220, 122. Sensor/detector/camera light filter—filter3—"tunes" light signal received by the sensor/detector/camera 1206 in the tissue imaging system.

According to this example, illumination light (e.g., such as in a visible light range of about wavelengths 400 nm to 760 nm that can be "tuned" by selection of a band-pass optical filter—filter 2—in the second light source 1222) can be selectively emitted from the second light source 1222, under control of the processor, responsive to computer instructions, operating in the information processing system 1812 (see FIG. 18). According to the example, FIG. 10 illustrates in an electromagnetic spectrum 1002 a range of wavelengths for this approximately "white" illumination light 1008.

In certain embodiments, the illumination light could be emitted in an alternative narrower range of wavelengths (e.g., such as in a visible light range of about wavelengths 470 nm to 760 nm that can be "tuned" by selection of a band-pass optical filter—filter 1—in the second light source 1222) shown in FIG. 10 as illumination light 1010. This alternative illumination light 1010 can serve to effectively illuminate the anatomical structures and tissue in the tissue region of interest 1202 with approximately "white" illumination light 1010, while substantially avoiding interference of any fluorescence light (e.g., wavelengths in a range of about 433 nm to about 450 nm) emitted from nervous tissue in the tissue region of interest 1202. In this example, FIG. 10 illustrates in an electromagnetic spectrum 1002 a range of wavelengths for the fluorescence light 1006 that may be emitted from the nervous tissue in response to illumination of the nervous tissue with the excitation light 1004. In certain embodiments, in which the illumination light is in a wider range of wavelengths for approximately "white" illumination light 1008, it can be seen in FIG. 10 that this wider range of wavelengths for illumination light 1008 overlaps with the range of wavelengths for the fluorescence light 1006. To avoid interference of approximately "white" illumination light 1008 in detection of the fluorescence light 1006 that may be emitted from the nervous tissue, an illumination light filter (filter 1) may include a notch filter that removes fluorescence light wavelengths 1006 from the approximately "white" illumination light 1008 emitted from the second light source 1222 and used to illuminate the tissue region of interest 1202.

The first light source 1220, according to the example, includes an LED light enclosure and one or more LED's therein that emit excitation light in the near UV light range. According to this example, an optical filter (filter 2) optically couples, and "tunes" the band-pass wavelength range of, the emitted excitation light from the LED light enclosure of the first light source 1220 to an optical fiber light concentrator lens 1224. A source optical train, in this example, comprises the output from the first light source 1220, the concentrator lens 1224, the one or more optical fibers 1210, and the light guide in the endoscope 1208, to thereby guide the excitation light to illuminate the tissue region of interest 1202. The processor can selectively turn the first light source ON or OFF, as well as control the level of luminance of the excitation light emitted out of the first light source 1220.

The second light source 1222, according to the example, includes an LED light enclosure and one or more LED's therein that emit illumination light, which in this example comprises "white" (or approximately white) light. According to this example, an optical filter (filter 1) optically couples, and "tunes" a band-pass wavelength range of, the illumination light from the LED light enclosure of the second light source 1222 to the optical fiber light concentrator lens 1224. The source optical train, in this example, comprises the second light source 1222, the concentrator lens 1224, the one or more optical fibers 1210, and the light guide in the endoscope 1208, to thereby guide the illumination light to illuminate the tissue region of interest 1202. The processor can selectively turn the second light source ON or OFF, as well as control the level of luminance of the illumination light emitted out of the second light source 1222.

In this example, light signal, whether comprising emitted light (fluorescence light) or reflected light or both, from the tissue region of interest 1202 is guided by one or more light guides in the flexible endoscope 1208 to a fiber-optic cable (fiber-optic light guide) 1211 and thereby to a filter—filter 3, a lens, and into the camera 1206. A receiving optical train, in this example, comprises one or more light guides in the flexible endoscope 1208, the fiber-optic cable 1211, the filter—filter 3, and the lens, which couple the light signal into the camera 1206. FIG. 14 shows a table of two example embodiments illustrating filter selection options for filters 1-3 as shown in FIG. 12, and as discussed above.

With reference again to FIGS. 1-4, in some embodiments, interrogation unit 120 comprises a plurality of cameras 122, each camera 122 of the plurality of cameras 122 optically coupled to one receiving optical train 117 of a corresponding plurality of optical trains 117. Various embodiments comprising more than one camera 122 may be useful for capturing light signals and displaying a stereoscopic visual image of a tissue region of interest 104.

FIG. 4 is a partial schematic diagram of a tissue imaging system 100 showing digital data paths in some embodiments. According to the example, a processor 142 comprises a data processor, such as a microprocessor, for processing digital inputs from, and delivering data and instructions to, various input/output devices, including excitation light source 102, illumination light source 103, camera 122, a user interface 146, a memory 145, a video recorder 160, and a visual display 150, in some embodiments. Processor 142 receives digital inputs from camera 122, user interface 146, and a memory 145. Depending on the embodiment of system 100, various suitable processors may be used as processor 142, including a medical-grade computer microprocessor such as currently used in existing medical imaging and computer-assisted imaging applications. In some embodiments, processor 142 is a plurality of microprocessors executing functions related to specific tasks, such as digital image processing and/or image enhancement, digital recording and memory management, excitation light source management, digital optical filtering of emitted and reflected light passing, user interface management, wireless communications, and other specific functions, in some embodiments.

Processor 142 executes a software package 144 residing on memory 145 and running on processor 142. In some embodiments, software package 144 is configured to conduct preferential visualization of a first tissue in a tissue region of interest, such as a nervous tissue, contrasted to a second tissue, such as a non-nervous tissue which may include for example adipose tissue, muscle tissue, connective tissue, and the like.

Processor 142 is configured to deliver instructions related to power delivery, aperture size and the like to camera 122 and to receive image data from camera 122, in some embodiments.

Memory 145 is a data storage device. Memory 145 may be configured as a writable memory or a combination of a writable memory and a read-only memory, in some embodiments.

Visual image data signals from processor 142 are received by visual display 150. Visual display 150 displays a visual image, such as a peripheral nerve on background tissue, to a surgeon or other user of system 100. Depending on the embodiment of the tissue imaging system 100, visual display 150 may be a standard video monitor, a high-resolution video monitor such as used during minimally invasive surgical procedures, or a computer monitor. Display 150 may be a light emitting diode (LED) display, including an organic LED (OLED), a liquid crystal display (LCD) a plasma display, a quantum dot display (QLED), or any medical-grade of other visual image display such as is currently used or shall be developed at a future time, without limitation.

Recordation and archiving of visual image data may be useful, such as for medical record keeping, teaching and instruction, and other uses. Accordingly, some embodiments of system 100 comprise a video recorder 160. Video recorder 160 receives visual image data from processor 142 and may output visual image data to visual display 150. A standard digital or analog (video tape) device may comprise video recorder 160, according to the embodiment of system 100.

User interface 146 is a means wherein a user of the tissue imaging system 100 interacts with and controls functions, including information exchange and instructions, and settings adjustments of various components and elements of the system 100. Some non-limiting examples of these functions include initiating or terminating power delivery to system 100 or any of its individual components, varying the intensity (luminosity) of excitation light 110 emitted from excitation light source 102; varying the wavelength of excitation light 110 through engaging optical or digital filters or by changing light sources, i.e., white light versus filtered (bandpass or other) of excitation light 110, and the like. Varying the pass-wavelength of a digital filter is varied, changed, or adjusted via user interface 146, in some embodiments. User interface 146 may comprise analog buttons or switches, digital input switches, a digital touchscreen, toggle switches, joysticks, wheels, whether digital or analog, or any combination thereof.

In some embodiments, user interface 146 comprises a plurality of user interfaces.

As a non-limiting example embodiment wherein user interface 146 is a plurality of user interfaces, system 100 may comprise a combination of (i) a graphical user interface residing on controller 140; (ii) button or other switches disposed on housing 121 of interrogation unit 120; (iii) a floor-based foot-activated toggle or other switch to change tissue illumination (i.e., excitation light 110) between white light and filtered light; and the like, in some embodiments.

Figure 5:
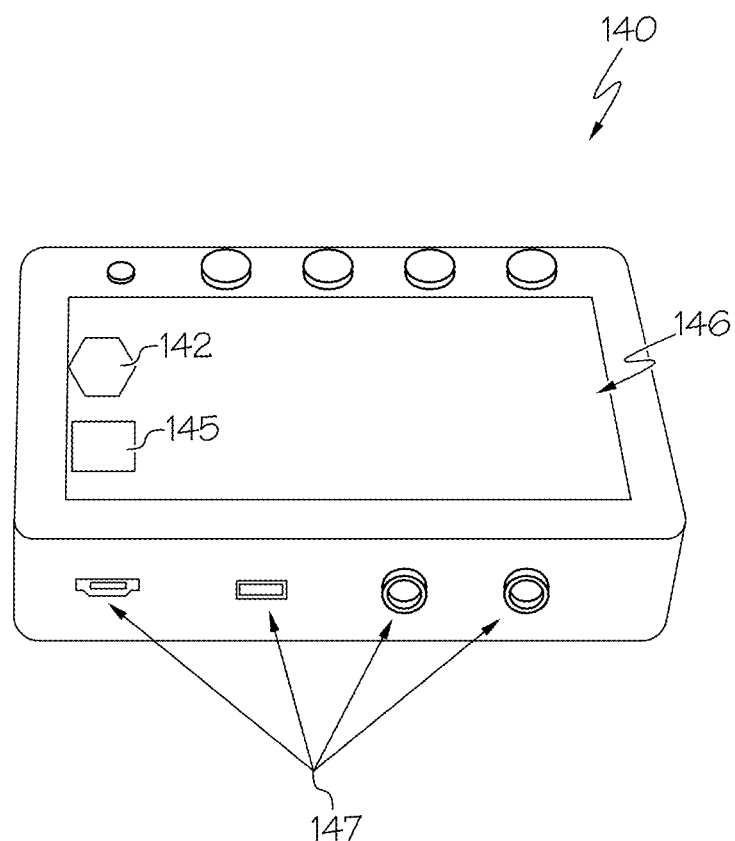
FIG. 5 is an illustration of a perspective view of an example controller unit suitable for use with a tissue imaging system, according to various embodiments.

FIG. 5 is a graphic illustration of an embodiment of a controller 140 for tissue imaging system 100. FIG. 5 shows controller 140 having processor 142, memory 145, and user interface 146. Also shown is a connection interface 147. Connection interface 147 may be a high-definition multimedia interface (HDMI), a set of external recording device input-output connectors, a universal serial bus (USB), and the like. In some embodiments, including the embodiment shown in FIG. 5, controller 140 comprises a plurality of connection interfaces 147. Connection interface(s) 147 may increase the functionality of system 100, for example, wherein the USB interface enables images to be stored on a USB storage medium and/or integrated with a medical-grade HIPAA recording device. Controller 140 comprises or is electrically coupled to a medical grade-compliant power source 152. In some embodiments, controller 140 comprises one or more wireless connection interface(s) 147, such as Bluetooth or WiFi wireless interface, for example, communicatively coupled to one or more (in any combination of) components forming the tissue imaging system 100 which may include but are not limited to excitation light source 102, illumination light source 103, source optical train 116, receiving optical train 117, camera 122, image display 150, and video recorder 160.

Figure 6:
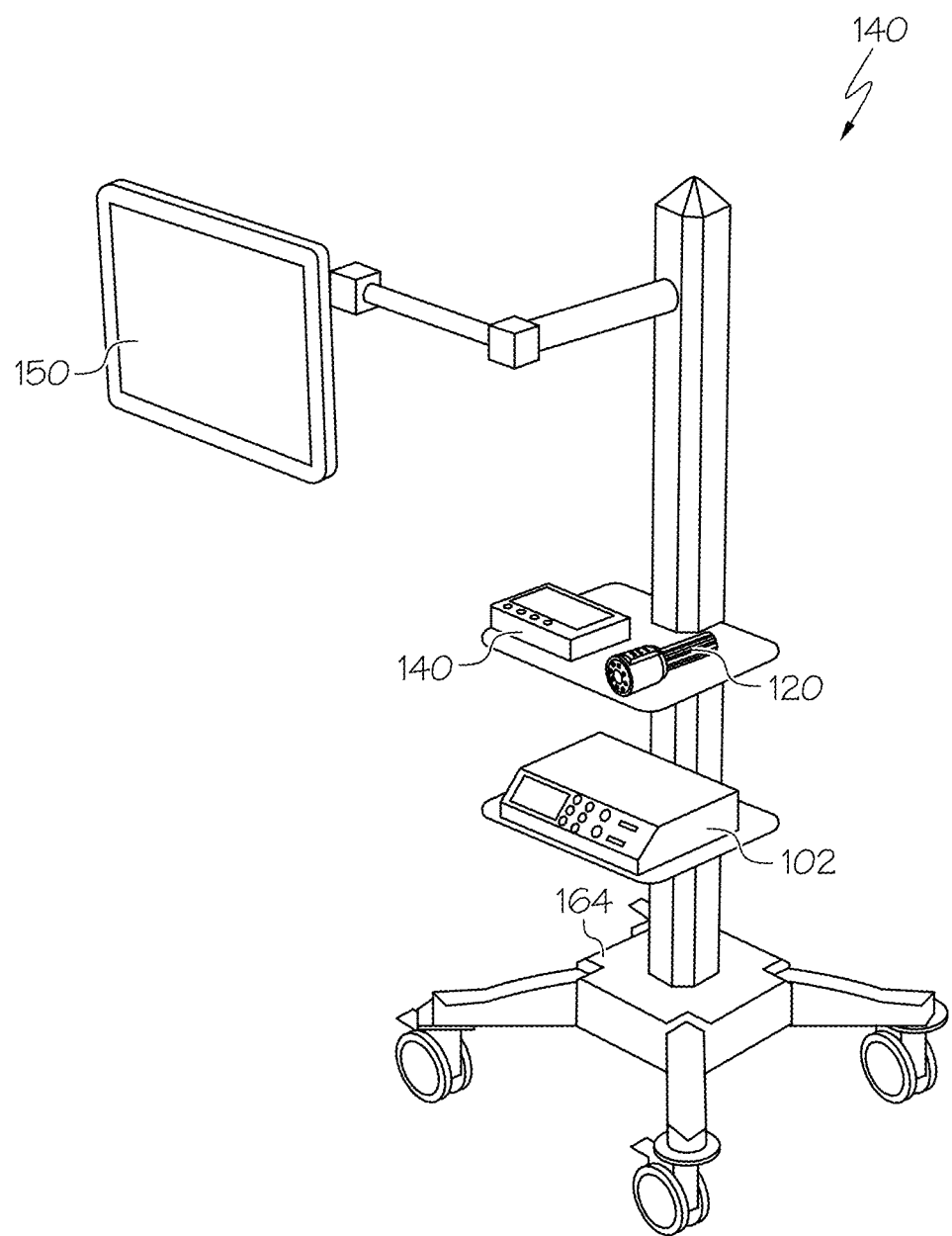
FIG. 6 is an illustration of an example tissue imaging system mounted on a medical cart.

FIG. 6 is an illustration of tissue imaging system 100 mounted on a medical cart 164. Medical cart 164 is, optionally, used to aggregate, mount, transport, and store one or more components of system 100, such as controller 140, excitation light source 102, video recorder 160, image display 150, and any related accessories, for example. In some embodiments, more than one medical cart 164 can be used to mount, transport, and/or store components of system 100. For example, in some embodiments, excitation light source 102 and illumination light source 103 are mounted on one medical cart 164, while the controller, along with other components, is mounted on a second medical cart 164.

Figure 7A:
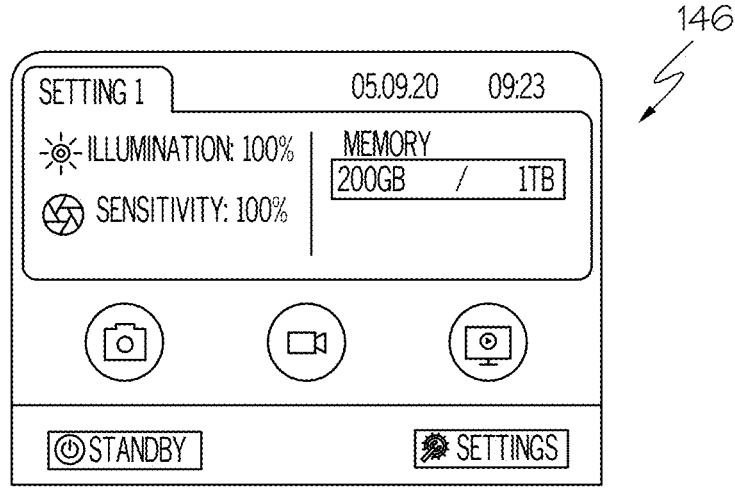
FIGS. 7A-7B are illustrations of an example user interface screen display of settings menus for an example tissue imaging system.

FIG. 7A is a front view of an embodiment of user interface 146 comprising a screen display showing an example of a main menu for tissue imaging system 100. Main menu may be displayed by user interface 146 as a screen located on controller 140 or a screen located on interrogation unit 120, in some embodiments. Main menu provides information to the user and permits the user to provide input controlling, setting, or adjusting elements of system 100, as discussed herein. For example, the main menu provides the user with information regarding an illumination setting, a sensitivity setting, status of memory for digital video storage, access to sub-menus and controls, and the like. Additional functionality of this illustrated embodiment includes a command to capture a photograph, initiate a video recording, transfer to a video screen showing a visual image of the operative field, or setting controller 140 to a standby mode.

Figure 7B:
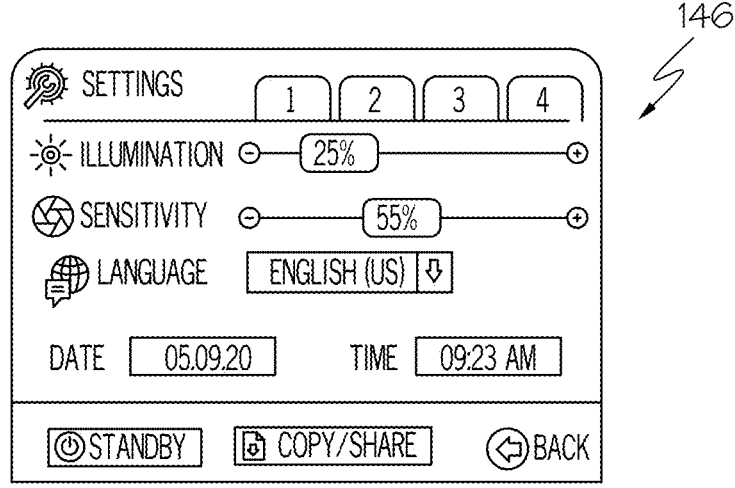

FIG. 7B is a front view of an embodiment of user interface 146 showing an example settings menu of system 100. This example display provides the user with options to select a language for menus displayed by user interface 146, adjust an illumination level setting of excitation light source 102, adjust a camera sensitivity setting, and provide an instruction to copy photos and video to a USB or other digital storage device, in some embodiments.

FIG. 8 is an example of image display 150 showing an image of a nervous tissue 802 and an image of non-nervous tissue 804 adjacent to or surrounding the nervous tissue 802, within a surgical field. A settings status indicator is also displayed as an inset within the surgical field tissue image display.

Figure 9:
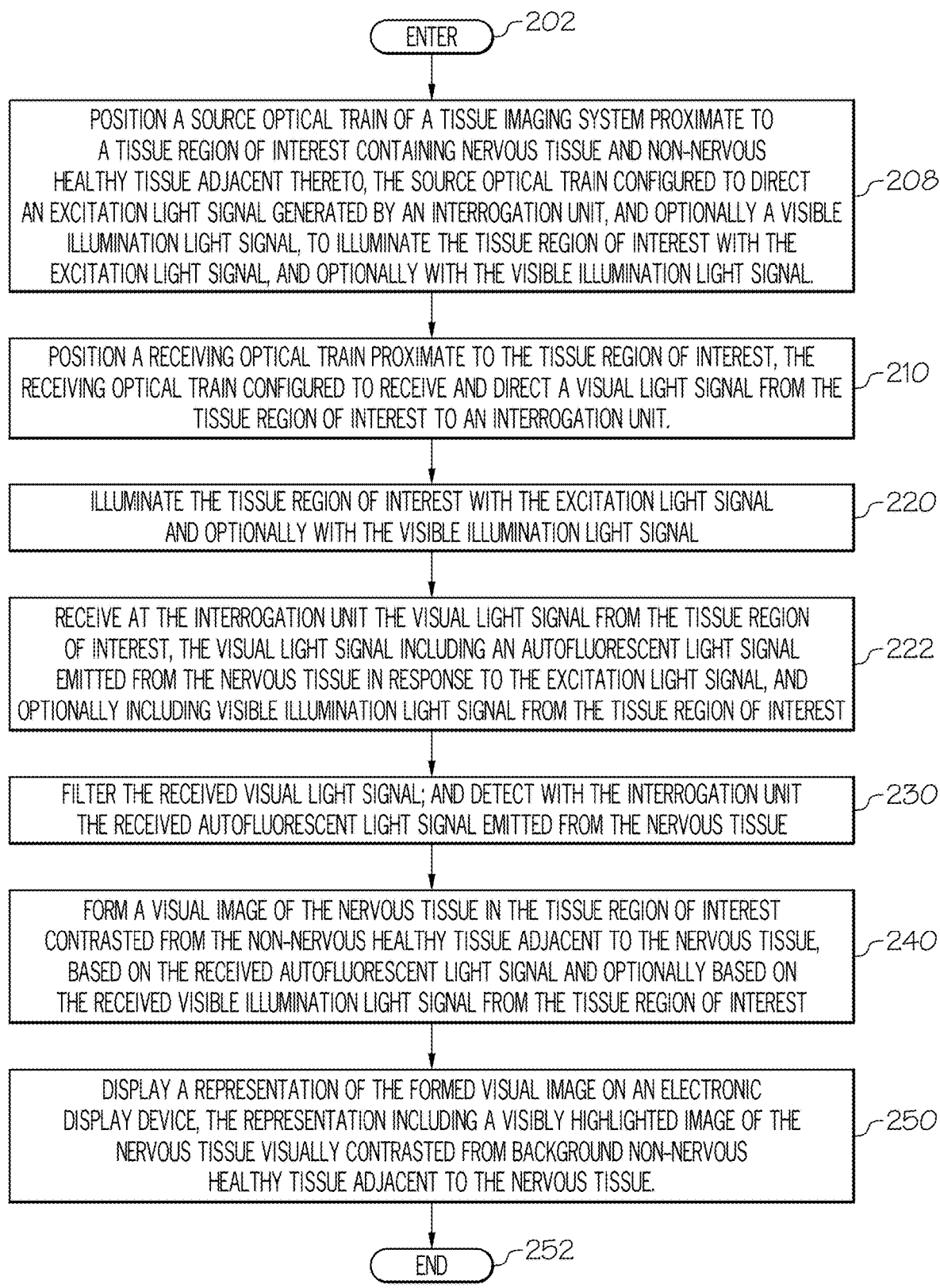
FIG. 9 is a flow diagram showing a method of use of an example tissue imaging system, according to various embodiments.

FIG. 9 is a flow diagram showing example process steps for a method of using a tissue imaging system. The method is entered at step 202. The method, in some embodiments, comprises positioning steps 208 and 210, an illuminating step 220, a receiving step 222, a detecting step 230, a visual image forming step 240, and a display image step. In some embodiments, detecting step 230 further comprises a filtering step.

Positioning steps 208 and 210, in some embodiments, comprise positioning an interrogation unit, the probe having a receiving optical train, configured to obtain data used to form a visual image proximate to a tissue region of interest containing healthy nervous tissue adjacent to or surrounded by healthy non-nervous tissue. In some embodiments, the tissue region of interest comprises a surgical wound. In some embodiments, the tissue region of interest comprises a surgical wound bed containing a portion of a spinal dura (e.g., duramadre), such as a portion of the thecal sac containing the spinal cord, anterior and posterior spinal nerves, and the dorsal spinal ganglia. In some embodiments, the formed visual image, at step 240, comprises an image of a healthy nervous tissue 802 (see the highlighted in bright white or other color image in FIG. 8), such as a nerve, a peripheral nerve, and/or duramadre, which is visually contrasted from adjacent and/or surrounding healthy non-nervous tissue 804 (much darker image contrasted from the highlighted image 802 in FIG. 8).

Illuminating step 220, in some embodiments, comprises illuminating the tissue with an excitation light comprising a first wavelength, in the absence of a day, a marker, or a probe, causing the tissue to generate an emitted light comprising a second wavelength in response to illumination with the excitation light of the first wavelength. In some embodiments, the first wavelength is a range of wavelengths. In some embodiments, the range of wavelengths is in the near-ultraviolet range. In some embodiments, the range of wavelengths is between about 300 nanometers (nm) and about 400 nm. In some embodiments, the wavelength of excitation light is about 370 nm. In some embodiments, the wavelength of the excitation light is a range of wavelengths between about 455 nm and about 510 nm. In some embodiments, the wavelength of the excitation light is about 485 nm. In some embodiments, the excitation light emanates from the interrogation unit.

Detecting step 230, in some embodiments, comprises detecting the emitted light from the tissue in the absence of a dye, a marker, or a probe. In some embodiments, a receiving optical train collects emitted light from the tissue, excitation light reflected from the tissue, and ambient light for filtering and processing.

Filtering step 235, in some embodiments, comprises filtering the emitted light. Filtering step 235 removes at least a portion of the reflected excitation light and at least a portion of the ambient light while preferentially allowing passage of a substantially larger portion of the emitted light. In some embodiments, filtering step 230 is performed by an optical filter. In some embodiments, the optical filter is comprised by a receiving optical train. In some embodiments, filtering step 230 comprises digital filtering of received light by a processor, such as a processor comprised by a controller and running a software package stored on a memory. In some embodiments, the digitally filtered light is received by a receiving optical train.

The forming step 240, in some embodiments, comprises forming a visual image of a nervous tissue, such as a peripheral nerve, which is contrasted and distinguished from an image of a non-nervous tissue adjacent to and/or surrounding the nervous tissue. The visual image is formed 240, in some embodiments, by processing of light received by an interrogation unit comprising a camera. In some embodiments, the light is digitally processed by the camera. In some embodiments, the light is digitally processed by a controller.

In some embodiments, the light is not digitally processed and the visual image is an optical image viewed through a lens. In some embodiments, the lens is comprised by a receiving optical train. The method is exited at step 252.

Alternative Example Embodiments of Tissue Imaging Systems

Figure 13:
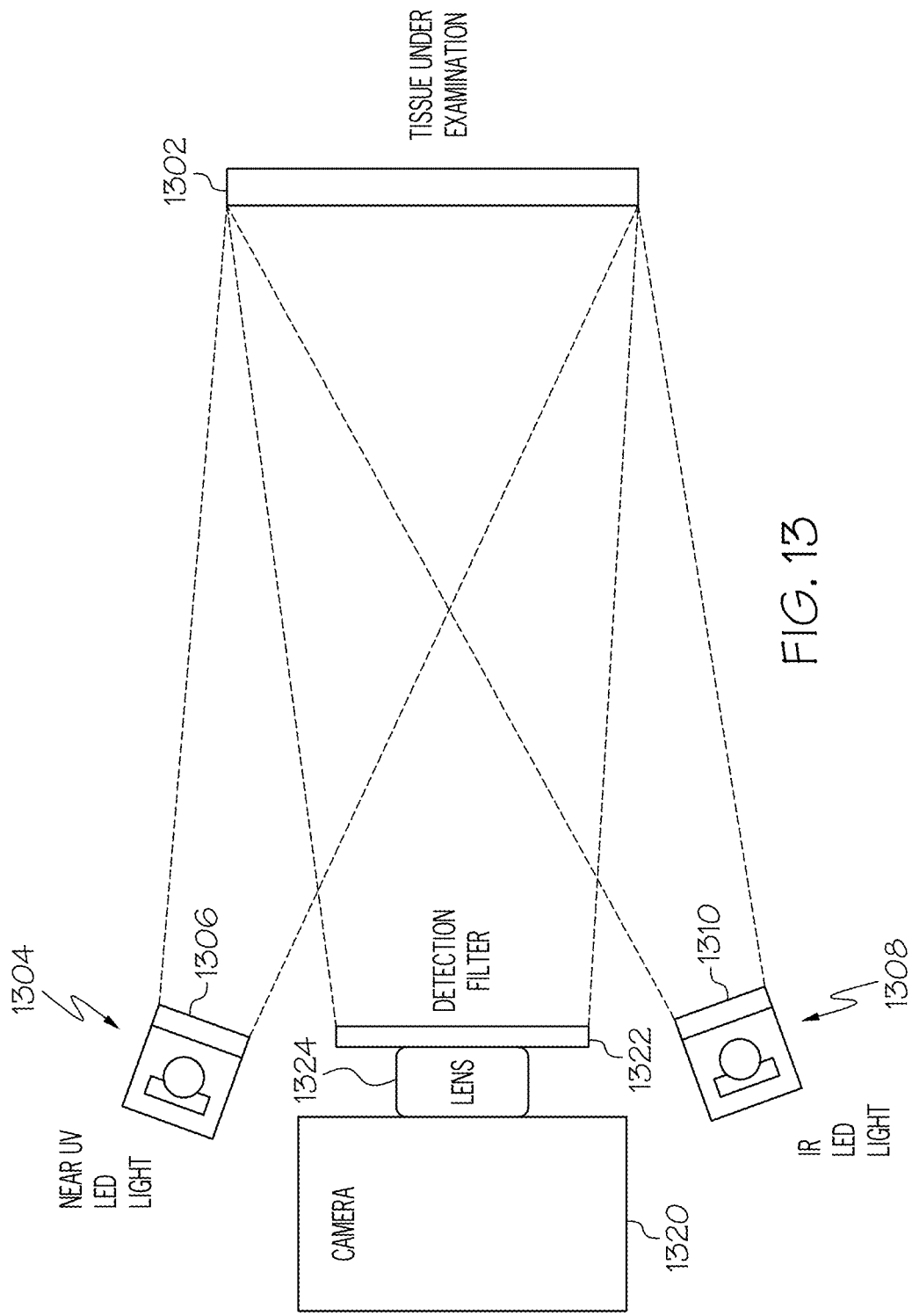
FIG. 13 is an illustration of several components of a second example tissue imaging system, according to various embodiments.

FIG. 13 illustrates an example embodiment of a tissue imaging system that selectively performs imaging of nervous tissue contrasted with imaging of non-nervous tissue using near UV illumination and alternatively, or contemporaneously, also can perform imaging of the tissue region of interest 1302 using infrared (IR) light. The inventors have noticed that perfusion of nervous tissue tends to be significantly lower than perfusion of non-nervous tissue. By selectively illuminating the tissue region of interest with IR light signals from an IR light source 1304, and detecting IR signals emitted from the tissue region of interest 1302, a formed image of nervous tissue in the tissue region of interest 1302 can be visibly contrasted with a formed image of non-nervous tissue in the tissue region of interest 1302. The formed image of the nervous tissue will typically be darker image (lower luminance) relative to the formed image of the non-nervous tissue (higher luminance). The two images can be visually contrasted with each other, such as on a display screen, to identify a location of nervous tissue relative to location of non-nervous tissue in the tissue region of interest 1302.

The near UV light source 1304 can include one or more optical filters 1306 to couple excitation light to a receiving optical train that, according to the example, includes a detection filter 1322, a lens 1324, and guiding light into the camera 1320. This set of components for a near UV excitation light and detection of endogenous autofluorescence light from nervous tissue contrasted to detection of light, if any, from non-nervous tissue, have a similar description to that already described above with respect to various example embodiments of tissue imaging system.

The IR light source 1308 can include one or more IR LED's and one or more optical filters 1310 to couple IR light to the tissue region of interest and therefrom couple IR light signal to the receiving optical train and to the camera 1320. The IR light detection, according to various embodiments, can be selectively performed either alternatively or concurrently with the detection of the endogenous autofluorescence light from nervous tissue contrasted to detection of light, if any, from non-nervous tissue. The two sets of images, one from the IR light detection and the other from the detection of endogenous autofluorescence light from nervous tissue, can be processed from the camera by a processing system which can overlay the images and render a display of overlaid images that show most likely locations of the healthy nervous tissue and of the healthy non-nervous tissue in the tissue region of interest 1302.

Enhancement of Tissue Imaging to Distinguish Nervous Tissue from Non-Nervous Tissue Adding Temperature Detection of Different Tissues The tip of an endoscopic probe coupled to the camera can temperature sensor (e.g., one or more IR detectors) capable of detecting the different temperatures of different issues in a tissue region of interest. Often, nervous tissue can be colder than non-nervous tissue because nervous tissue does not contain (or perfuse) blood as do veins, arteries, and muscles in non-nervous tissue. Because of the temperature difference between nervous tissue and non-nervous tissue, vascularized tissue will shine a different color so that the nerves and duramadre can be differentiated from adjacent and/or surrounding non-nervous tissue structures. The intrinsic temperatures of the various tissues in a tissue region of interest can be measured using a temperature sensor equipped endoscopic probe e.g., using one or more temperature sensors strategically located about the outer surface of the endoscopic probe tip). A thermal potential difference is measured across the tissue region of interest, and a temperature map thereof can be generated. This map highlights major temperature transitions between adjacent non-nervous tissue structures and the nervous tissue. The nervous tissue can be additionally contrasted with adjacent or surrounding non-nervous tissue, using tissue imaging by detecting endogenous autofluorescence of the nervous tissue which is contrasted against the light signal received from non-nervous tissue in the tissue region of interest. The processing system then can combine e.g., overlay) the endogenous autofluorescence images with the temperature map of the various tissues in the tissue region of interest. This can form a composite image of the tissue region of interest in which a first composite image of nervous tissue can be contrasted with a second composite image of the non-nervous tissue. This combination of thermal mapping and endogenous autofluorescence imaging over the same tissue region of interest can increase a sensitivity and specificity in a detection process used by the processing system to better discriminate between nervous tissue and non-nervous tissue in the tissue region of interest. This combination detection process enhances the identification of nervous tissue as contrasted with identification of non-nervous tissue for a tissue imaging system.

Utilizing Impedance and Depolarization Analysis

Nerves have a basal emission of energy when excited by white light that can be detected by the human eye on a display. When shining near ultraviolet light, a different depolarization wave is generated that can be detected by a special sensor which in turn transforms the moving depolarization wave into noise or vibration alerting the surgeon to a proximity of the nervous tissue before the human eye can visualize the nervous tissue on a display.

This detection can be combined with one or more of the they mapping and endogenous autofluorescence imaging detection processes described above to enhance sensitivity and specificity in a detection process used by the processing system to better discriminate between nervous tissue and non-nervous tissue in the tissue region of interest.

Utilizing Impedance and Depolarization From Contactless Electrical Stimulation Combined With Analysis of Changing Endogenous Autofluorescence Light Signal Nerves can be induced to generate a moving depolarization wave (e.g., a moving pulsed electrical signal) that travels along the axon of a nervous tissue, in response to a pulsed oscillating/changing electrical field generated in proximity to the nervous tissue. The pulsed oscillating/changing electrical field can be generated in various different ways. In one example, a driving coil can be located near a tip of an endoscopic probe coupled to the camera. An oscillating electrical signal applied to the driving coil can generate a pulsed oscillating/changing electrical field in proximity to the nervous tissue. This moving pulsed electrical signal traveling along the axon of a nervous tissue can be detected by electronic pick-up sensors, or other electrical signal detection circuitry, even without making physical contact with the nervous tissue. Non-nervous tissue does not respond (with a moving depolarization wave) to the pulsed oscillating/changing electrical field.

It is anticipated that the moving depolarization wave along the axon would also temporarily change the endogenous autofluorescence effect of the nervous tissue at the wave front of the moving depolarization wave. The changed endogenous autofluorescence effect at the moving wave front (at one point in the axon) would be temporarily different from the endogenous autofluorescence effect along the remainder of the axon. The nervous tissue (with a moving depolarization wave front along an axon of the nervous tissue) would exhibit a changing wavelength (and possibly a changing luminance) of an endogenous autofluorescence light signal emitted from the nervous tissue at the wave front that is different from endogenous autofluorescence light signal emitted from the nervous tissue at other portions of the axon. That is, the autofluorescence light signal emitted from the nervous tissue would temporarily change its wavelength and possibly change its intensity, following the depolarization wave front moving along the axon of the nervous tissue.

This change in the autofluorescence light signal can be correlated to the pulsed oscillating/changing electrical field signals driving the moving depolarization wave fronts along the axon. Additionally, the detection of this pulsing (changing) autofluorescence light signal could be captured by the camera in a series of sequential images of the tissue region of interest. The series of sequential images could be analyzed real-time, or nearly real-time, by a processing system using image processing. From the analysis the processing system can generate an approximate map of a path of the axon in proximity to the moving wave front of depolarization waves. This map of the path of the nervous tissue (along the axon) can show an image of nervous tissue and a separate image of non-nervous tissue. These images can alert a surgeon to a location of the nervous tissue and of the non-nervous tissue in the tissue region of interest.

This detection of changing autofluorescence light signal to map a location of an axon of the nervous tissue can be combined with one or more of the thermal mapping and endogenous autofluorescence imaging detection processes described above to enhance sensitivity and specificity in a detection process used by the processing system to better discriminate between nervous tissue and non-nervous tissue in the tissue region of interest. A surgeon, with reference to the images of the nervous tissue and the non-nervous tissue adjacent to or surrounding the nervous tissue, would be guide to a location of the nervous tissue and of the non-nervous tissue in the tissue region of interest.

EXAMPLES

The foregoing description of various embodiments of the invention is demonstrated, in part, by the examples listed below.

Example 1—Head and Neck Tumors

Case 1: A 35-year-old woman presented with a painless, slowly-growing nodule in the left lateral face that, on palpation, felt soft and non-moveable, was non-tender, and measured 3 cm in maximum diameter. The patient's neurological examination was entirely normal, including no evidence of facial paralysis. Ultrasound revealed a solid hypoechoic nodule in the left parotid gland. Fine needle aspiration (FNA) was performed, which revealed a benign pleomorphic adenoma.

Case 2: A 55-year-old woman presented with a painless, slowly-growing nodule in the left lateral face that, upon palpation, felt firm and rubbery, was non-tender, and measured 2.5 cm in maximum diameter. As with the previous case, the patient's neurological examination was normal, ultrasound revealed a solid hypoechoic nodule in the left parotid gland, and FNA revealed a benign pleomorphic adenoma.

Case 3: A 43-year-old woman presented with a painless, slowly-growing nodule in the right lateral, lower face, in the area of the lower pole of the parotid gland. On palpation, the nodule felt firm and non-mobile, was non-tender, and measured 4 cm in maximum diameter. On CT scan, the lesion was well defined and well-encapsulated. Fine needle aspiration revealed both myoepithelial and mesenchymal components consistent with a pleomorphic adenoma.

A total parotidectomy was performed in each of cases 1-3, described above, using a tissue imaging system for enhanced intra-operative visualization of the facial nerve and its branches. An Avelino-Gutierrez incision was used for each patient. A superficial cervical-fascial flap was created between the superficial musculoaponeurotic system layer and the parotid fascia until the anterior border of the parotid gland was visible. At this point, the facial nerve trunk was identified, and dissection of the facial nerve branches was performed using the tissue imaging system to permit visualization of the surgical field under near-ultraviolet (NUV) light. Under NUV light, the cervicofacial and temporofacial branches and lengths of these branches auto-fluoresced brightly and, hence, were clearly identified. In all three patients, the parotidectomy was completed and a drain placed without intra-operative complications, and both the immediate-postoperative and post-operative day #1 neurological examinations remained normal. All three patients were discharged to their homes on the first post-operative day and remained without complications or neurological deficits at the time of their final surgery clinic visit.

Example 2—Thyroid Carcinoma

Case 4: A 45-year-old female patient was referred to our clinic with a 1.1 cm subcutaneous nodule laterally positioned on the right side of the neck. Physical examination revealed a firm, painless nodule in the area of the right lobe of the thyroid, which moved up and down when the patient swallowed. On ultrasound, a solid 11×20 mm nodule was visualized that was irregular in shape, with numerous small calcifications and an unclear border. Serum thyroglobulin was elevated. On FNA, papillary thyroid carcinoma diagnosed, after which further imaging revealed disseminated metastases consistent with Bethesda stage IV. Surgical removal of the thyroid and central and lateral neck dissection were performed. During the former, both the recurrent laryngeal and hypoglossal nerve fluoresced brightly under NUV light and were easily avoided. During neck dissection, all nerves within the surgical field again were clearly identified throughout their course under NUV, and this degree of visualization was clearly superior to that achieved under white light.

Example 3—Neurosurgery

Case 5: A previously healthy 88-year-old male was referred for severe low back pain that limited his walking to roughly 500 meters before he had to rest. His baseline examination revealed exquisite tenderness in the low back over the L4 spinous process, but no neurological deficits. Both CT and MRI revealed tumor infiltration into and resultant destruction of the $4^{th}$ lumbar vertebra, along with soft tissue infiltration into the epidural space. A trans pedicular percutaneous biopsy was performed that revealed non-Hodgkin's B-cell lymphoma. After discussing various options, a decision was made to perform two-stage spinal surgery prior to initiating chemotherapy: the first stage to decompress the spinal canal; the second stage to reconstruct and stabilize the lumbar spine.

Surgery was performed under general anesthesia using a mini-open retroperitoneal approach with the patient placed in a right lateral decubitus position. The procedure then was performed in a 360° (ventro-dorsal) fashion, including instrumentation, and entailed posterior percutaneous instrumentation from L2 through to the sacrum. For the second step involving resection of the L4 vertebral body, both the L3-4 and L4-5 intervertebral discs and tumor tissue located ventrally in the spinal canal were resected followed by reconstruction of the anterior column using a titanium mesh prosthesis. A left-sided anterolateral approach was adopted. The patient experienced neither intra-operative nor postoperative complications and, other than wound discomfort, was pain free postoperatively. He left the hospital three days after the second surgery and started chemotherapy within one week. He remained fully ambulatory and pain free.

Case 6: During a difficult delivery, a baby suffered a right brachial plexus injury. At six months of age, she was brought into the clinic by her parents exhibiting both shoulder and elbow flexion palsy, and was scheduled for surgical reconstruction using a sural nerve graft harvested from the contralateral lower limb to replace the affected part of the brachial plexus and the suprascapular nerve. Under NUV light, the contralateral sural nerve, and the ipsilateral brachial plexus, phrenic nerve and suprascapular nerve all were easily visualized throughout their course in the surgical field. The surgery proceeded without complication, and the child is currently in rehabilitation.

A tissue imaging system has been described herein. The tissue imaging system produces a visual image, either optically or digitally, such as of a surgical field, wherein visualization of a target tissue region of interest can include a formed highlighted image of nervous tissue in the tissue region of interest, such as a peripheral nerve or spinal dura (duramadre), which is enhanced by endogenous autofluorescense or other intrinsic property of the nervous tissue, such as the peripheral nerve or spinal dura (duramadre), in response to illumination with excitation light. The produced visual image includes the formed highlighted image of nervous tissue, and a formed darker image of a non-nervous tissue adjacent to and/or surrounding the nervous tissue. Filtering of the excitation light, emitted light, reflected light, or a combination thereof enhances the visual image by further distinguishing the target tissue structure from surrounding adipose, muscle, or connective tissue. Use of excitation light in the NUV wavelength range between about 300 nm and about 400 nm is particularly effective.

Prophetic Example Applications for a Tissue Imaging System, As Discussed Above

Thyroidectomy

Once the thyroidectomy has begun and the lobe of the thyroid gland is exposed and the superior pedicle is ligated, the parathyroid gland is identified. Close to it the recurrent laryngeal nerve needs to be found to continue the dissection. The laryngeal nerve is at risk of being injured. The assistant surgeon positions the Dendrite camera at approximately 20 cm from the surgical field which will illuminate the nerve (healthy nervous tissue) and obtain an autofluorescence image of its entire trajectory.

Guided by autofluorescence from the nerve contrasted from light emitted or reflected by healthy non-nervous tissue adjacent to and/or surrounding the healthy nervous tissue, the surgeon dissects and separates the recurrent nerve from the surroundings structures The Dendrite camera can differentiate the nerve from adjacent normal structures (healthy non-nervous tissue) by means of illumination with light at specific excitation wavelength range. The excitation light may be generated and emitted using one or more optical filters that are incorporated with the light source in the imaging system. At the same time, a processor, operating in response to software, can analyze the different images formed from received light signals from the tissue region of interest, blocking or significantly reducing intensity of light signals that are not fluorescence light emitted from the nervous tissue and increasing the resolution of the structures (nervous tissue) that shine fluorescence light at certain wavelengths such as the emitted light signals from nervous tissue, e.g., from the nerve.

Robotic Prostatectomy

The 30° angle-down lens that is part of the robotic platform is used for the bladder neck dissection. The anterior bladder neck is divided, and the ureteral orifice position and presence of a median lobe were assessed, and then the posterior bladder neck is divided. The vas deferens and seminal vesicles are then identified. The vasa are divided and the seminal vesicles are dissected in a cautery-free manner to avoid potential injury to the neurovascular bundles. The posterior layer of Denonvillier's fascia was divided allowing for identification of perirectal fat, which served as a guide between the prostate and rectum. To optimize nerve sparing the surgeon switches between white light and near ultraviolet light utilizing the Dendrite camera (e.g., utilizing a Dendrite adaptor attached to the rigid endoscope of the robotic arm) which allows a surgeon to see images of the healthy nervous tissue in a tissue region of interest and differentiate the healthy nervous tissue from normal healthy non-nervous tissue. Utilizing the dual mode combining white light and NUV light the lateral prostatic fascia is incised on each side allowing the surgeon to visualize the neurovascular bundles (nervous tissue) from the normal non-nervous tissues adjacent to and/or surrounding the nervous tissue, to fall posterolaterally, and a bilateral nerve-sparing procedure is performed.

The neurovascular bundle that can be seen and differentiated from healthy non-nervous tissue when using the NUV light, is released distally to the level of the urethra and prostatic apex. At this point, the only remaining attachments of the prostate were the dorsal vein complex (DVC) and the urethra. The DVC and urethra are then divided rendering the prostate free, and the specimen is placed in a 10-mm endo-catch bag.

Laparoscopic Nissen Fundoplication

The surgeon accessed the abdominal cavity laparoscopically and after insufflating with CO2, the upper abdomen can be visualized. The gastroesophageal junction is identified and to avoid injury to the vagal nerves that can result in severe gastroparesis, the surgeon utilizes the Dendrite camera with NUV light to identify the anterior and posterior vagal nerves and differentiate those from other normal healthy non-nervous soft tissues and vascular structures. This maneuver becomes even more important when surgeons are re-operating this area and the tissues are glued to each other due to scar tissue. Here the camera armed with NUV light can identify and follow the nerve preventing it from being severed.

Laparoscopic/Open Inguinal Hernia Repair

When operating in the groin of a patient with an open technique, the surgeon dissects the cord structures with white light in order to identify the hernia sac. While dissecting the cord the surgeon can hold in his hand, or attach to a special arm the open Dendrite camera (e.g., using a Dendrite adaptor attached to the rigid endoscope) and switch from white light to NUV light using the Dendrite camera in order to identify the genital branch of the genitofemoral nerve as well as the ilio-inguinal nerves (nervous tissues) preventing those from being transected by the surgeon or being included in the implanted mesh. Both could result in loss of sensation or long term disabling groin pain. When operating laparoscopically, the Dendrite camera using an adaptor is attached to the laparoscope that is projected to a display monitor and allows the surgeon to visualize the images of the same structures in the tissue region of interest and thereby prevent those nervous tissues from being injured or trapped by mesh.

Open/Laparoscopic/Robotic Pelvic Surgery

When operating in the pelvic region (for example, in a colorectal surgery, gynecological or urological procedures), either open by using the handheld Dendrite camera device, or laparoscopically by using the Dendrite camera with an adaptor attached to the endoscope or robotically, attaching the Dendrite camera adaptor to the robotic arm, the surgeon can dissect and remove anatomical structures utilizing the NUV light of the Dendrite camera identifying and protecting nerves (nervous tissue) by differentiating it from the normal healthy non-nervous tissue adjacent to and/or surrounding the nervous tissues.

Open Heart and Open/Thoracoscopic Lung Surgery

Phrenic nerve injury following cardiac surgery is variable in its incidence depending on the diligence with which it is sought. Definitive studies have shown this complication to be related to cold-induced injury during myocardial protection strategies and possibly to mechanical injury during internal mammary artery harvesting. The consequences are also variable and depend to a large extent on the underlying condition of the patient, particularly with regard to pulmonary function. The response of the patient may range from an asymptomatic radiographic abnormality to severe pulmonary dysfunction requiring prolonged mechanical ventilation and other associated morbidities and even mortality. When harvesting the mammary artery and/or opening the pericardium (adjacent to and/or surrounding nervous tissue), the surgeon uses either the handheld open Dendrite camera that is attached to a special arm or the thoracoscopic Dendrite camera with adaptor that is attached to a thoracoscope to visualize the phrenic nerve (nervous tissue) and protect it from being transected when harvesting the mammary artery.

Surgery of the Upper and Lower Extremities

When conducting vascular, neurosurgical, plastic and/or orthopedic procedures, the surgeon will place a large skin incision to access the anatomical compartment in order to carry out the final procedure. While doing so the surgeon needs to differentiate between nerves (nervous tissue) and normal muscular and vascular structures (non-nervous tissue adjacent to and/or surrounding nervous tissue). By holding the Dendrite camera on a special arm or holding it by an assistant, the surgeon can shine NUV light emitted by the Dendrite camera and identify the nerves (nervous tissue) and differentiate those from the normal surrounding soft tissues and vascular structures (non-nervous tissue adjacent to and/or surrounding nervous tissue).

Neurosurgical Procedures

Using a Dendrite camera with a universal adapter attached to a microscope, the interaction between the images provided by the NUV camera and the real time images captured by the microscope enables the surgeon to individualize neural structures (healthy nervous tissue) involved or surrounded by healthy non-nervous tissue and/or tumorous processes such as meningeomas, metastasis, neurinomas, etc. In combination with temperature and flow detectors the NUV Dendrite camera visualization of images of healthy nervous tissue contrasted from adjacent and/or surrounding healthy non-nervous tissue, offers the surgeon the potential to access sensible areas like the cavernous sinus, remove the invading process, and exit with minimal healthy tissue disruption is unlimited.

Skull Base Surgery

Processes invading the skull base that invade or disrupt the dura mater (duramadre) are difficult to resect. Using the NUV Dendrite camera the recognition of the dura (nervous tissue) quickens up the dissection and resection, enabling the surgeon even to resect "among healthy borders" (healthy non-nervous tissue adjacent to and/or surrounding nervous tissue) as in general surgery.

Spine Surgery

The use of the Dendrite camera can identify duramadre (healthy nervous tissue) by imaging of nervous tissue contrasted to adjacent and/or surrounding healthy non-nervous tissue, which offers the surgeon maximum potential for successful procedure when using the Dendrite camera in spine surgery.

Percutaneous Endoscopic Discectomy

Using the Dendrite camera with an adaptor to an endoscope, when approaching the spine endoscopically provides the surgeon with immediate tissue imaging feedback of the location of the nerve root (indirectly by recognizing the dura mater cover of the nerve) (healthy nervous tissue) as contrasted to the location of adjacent and/or surrounding healthy non-nervous tissue, thus enabling a clear dissection from the surrounding yellow ligament and disc or bone material.

Thoracoscopic Sympathectomy

NUV images using a Dendrite camera (e.g., using a Dendrite adaptor attached to the rigid endoscope) shows the surgeon immediately the location of the sympathetic chain and its collateral fibers (nervous tissue) as contrasted to the location of adjacent and/or surrounding healthy non-nervous tissue. This accurate location of the nervous tissue and the non-nervous tissue is very important when performing sympathectomy for hyperhidrosis.

Thoracoscopic Discectomy

The use of NUV illumination and a Dendrite camera (e.g., using a Dendrite adaptor attached to the rigid endoscope) in the chest cavity gives the surgeon important information about the location of the sympathetic fibers (nervous tissue) as contrasted to the location of adjacent and/or surrounding healthy non-nervous tissue, before entering the spinal canal and the dura mater after opening the canal and can successfully decompress the spinal cord.

Non-Limiting Examples

The present invention may be implemented as a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a Memory Stick®, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk®, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, implement the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the functions/acts specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although the present specification may describe components and functions implemented in the embodiments with reference to particular standards and protocols, the invention is not limited to such standards and protocols. Each of the standards represents examples of the state of the art. Such standards are from time-to-time superseded by faster or more efficient equivalents having essentially the same functions.

The illustrations of examples described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this invention. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. The examples herein are intended to cover any and all adaptations or variations of various embodiments. Combinations of the above embodiments, and other embodiments not specifically described herein, are contemplated herein.

The Abstract is provided with the understanding that it is not intended be used to interpret or limit the scope or meaning of the claims. In addition, in the foregoing Detailed Description, various features are grouped together in a single example embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

Although only one processor is illustrated for an information processing system, information processing systems with multiple central processing units (CPUs) or processors can be used equally effectively. Various embodiments of the present invention can further incorporate interfaces that each includes separate, fully programmed microprocessors that are used to off-load processing from the processor. Additionally, various embodiments can include an input user interface, and an output user interface, or both. Examples of input user interfaces can include, for example and not for limitation, a mouse, a keyboard, a keypad, a touchpad, or a microphone for receiving uttered voice commands and input data. Examples of output user interfaces can include, for example and not for limitation, a display, lights, lamps, tactile output devices, or a speaker for outputting audible signals and/or voice responses to received uttered voice commands and input data.

An operating system included in main memory for a processing system may be a suitable multitasking and/or multiprocessing operating system, such as, but not limited to, any of the Linux®, UNIX®, Windows®, and Windows® Server based operating systems. Various embodiments of the present invention are able to use any other suitable operating system. Various embodiments of the present invention utilize architectures, such as an object oriented framework mechanism, that allow instructions of the components of the operating system to be executed on any processor located within an information processing system. Various embodiments of the present invention are able to be adapted to work with any data communications connections including, but not limited to, present day analog and/or digital techniques, via wired communication, via wireless communication, via short range wireless communication, via long range wireless communication, via optical communication, via fiber optics communication, via satellite communication, or via a future networking mechanism.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "another", as used herein, is defined as at least a second or more. The terms "including" and "having," as used herein, are defined as comprising (i.e., open language). The term "coupled," as used herein, is defined as "connected," although not necessarily directly, and not necessarily mechanically. "Communicatively coupled" refers to coupling of components such that these components are able to communicate with one another through, for example, wired, wireless or other communications media. The terms "communicatively coupled" or "communicatively coupling" include, but are not limited to, communicating electronic control signals by which one element may direct or control another. The term "configured to" describes hardware, software or a combination of hardware and software that is set up, arranged, built, composed, constructed, designed or that has any combination of these characteristics to carry out a given function. The term "adapted to" describes hardware, software or a combination of hardware and software that is capable of, able to accommodate, to make, or that is suitable to carry out a given function.

The terms "controller", "computer", "processor", "server", "client", "computer system", "computing system", "personal computing system", "processing system", or "information processing system", describe examples of a suitably configured processing system adapted to implement one or more embodiments herein. Any suitably configured processing system is similarly able to be used by embodiments herein, for example and not for limitation, a personal computer, a laptop personal computer (laptop PC), a tablet computer, a smart phone, a mobile phone, a wireless communication device, a personal digital assistant, a workstation, and the like. A processing system may include one or more processing systems or processors. A processing system can be realized in a centralized fashion in one processing system or in a distributed fashion where different elements are spread across several interconnected processing systems.

The corresponding structures, materials, acts, and equivalents of all means or step plus function elements in the claims below are intended to include any structure, material, or act for performing the function in combination with other claimed elements as specifically claimed.

The description of the present application has been presented for purposes of illustration and description, but is not intended to be exhaustive or limited to the invention in the form disclosed. Many modifications and variations will be apparent to those of ordinary skill in the art without departing from the scope of the invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. A method for a nervous tissue imaging system, the method comprising:

selectively turning ON an excitation light source;
   optically coupling excitation light, from the excitation light source into a source optical train, and optically filtering the excitation light to only pass excitation light signals in a first wavelength range from 365 nm to 400 nm, and directing emitted excitation light from the source optical train to uniformly illuminate a tissue region of interest causing healthy nervous tissue in the tissue region of interest, in response to being illuminated with the excitation light, to endogenously autofluoresce and emit first autofluorescence light at a first luminance in a second wavelength range from 433 nm to 450 nm;
   selectively turning ON an illumination light source;
   optically coupling illumination light, from the illumination light source into a second source optical train, and optically filtering the illumination light to only pass illumination light signals of wavelengths outside of the first wavelength range and outside of the second wavelength range, thereby emitting visible illumination light from the second source optical train, and directing the emitted visible illumination light from the second source optical train to illuminate the tissue region of interest in the surgical field on the patient's body; and
   receiving, by a receiving optical train, light signals including the first autofluorescence light emitted from healthy nervous tissue in the tissue region of interest, and optically filtering the received light signals to only pass light signals of wavelengths in the second wavelength range, and optically coupling the optically filtered received light signals into a camera device.

2. The method of claim 1, comprising:
   capturing, by the camera device, image data of the optically filtered received light signals including the first autofluorescence light emitted from the healthy nervous tissue and received by the receiving optical train.

3. The method of claim 2, comprising:
   displaying an image real-time on a display screen based on the captured image data, showing the healthy nervous tissue contrasted to healthy non-nervous tissue surrounding the healthy nervous tissue in the tissue region of interest in the surgical field on the patient's body.

4. The method of claim 2, comprising:
   performing image processing of the captured image data from the camera device;
   overlaying an image of the first autofluorescence light emitted from the healthy nervous tissue and an image of surrounding healthy non-nervous tissue in the tissue region of interest to create a composite image of the tissue region of interest; and
   displaying the composite image real-time on a display screen showing the healthy nervous tissue contrasted to healthy non-nervous tissue surrounding the healthy nervous tissue in the tissue region of interest in the surgical field on the patient's body.

5. The method of claim 1, wherein the first wavelength range is from 382 nm to 392 nm.

6. A method for a nervous tissue imaging system, the method comprising:
   selectively turning ON an excitation light source;
   optically coupling excitation light, from the excitation light source into a source optical train, and optically filtering the excitation light to only pass excitation light signals in a first wavelength range from 365 nm to 400 nm, and directing emitted excitation light from the source optical train to uniformly illuminate a tissue region of interest causing healthy nervous tissue in the tissue region of interest, in response to being illuminated with the excitation light, to endogenously autofluoresce and emit first autofluorescence light at a first luminance in a second wavelength range from 433 nm to 450 nm; and receiving, by a receiving optical train, light signals including the first autofluorescence light emitted from healthy nervous tissue in the tissue region of interest, and optically filtering the received light signals to only pass light signals of wavelengths in the second wavelength range, and optically coupling the optically filtered received light signals into a camera device.

7. The method of claim 6, comprising:

capturing, by the camera device, image data of the optically filtered received light signals including the first autofluorescence light emitted from the healthy nervous tissue and received by the receiving optical train.

8. The method of claim 7, comprising:

displaying an image real-time on a display screen based on the captured image data, showing the healthy nervous tissue contrasted to healthy non-nervous tissue surrounding the healthy nervous tissue in the tissue region of interest in the surgical field on the patient's body.

9. The method of claim 7, comprising:

performing image processing of the captured image data from the camera device;

overlaying an image of the first autofluorescence light emitted from the healthy nervous tissue and an image of surrounding healthy non-nervous tissue to create a composite image of the tissue region of interest; and displaying the composite image real-time on a display screen showing the healthy nervous tissue contrasted to healthy non-nervous tissue surrounding the healthy nervous tissue in the tissue region of interest in the surgical field on the patient's body.

10. The method of claim 6, wherein the first wavelength range is from 382 nm to 392 nm.

11. A method for a nervous tissue imaging system, the method comprising:

selectively turning ON an excitation light source;

optically coupling excitation light, from the excitation light source into a source optical train, and optically filtering the excitation light to only pass excitation light signals in a first wavelength range from 365 nm to 400 nm, and directing emitted excitation light from the source optical train to uniformly illuminate a tissue region of interest causing healthy nervous tissue in the tissue region of interest, in response to being illuminated with the excitation light, to endogenously autofluoresce and emit first autofluorescence light at a first luminance in a second wavelength range from 433 nm to 450 nm;

selectively turning ON an illumination light source;

optically coupling illumination light, from the illumination light source into a second source optical train, and optically filtering the illumination light to only pass illumination light signals of wavelengths longer than the second wavelength range, thereby emitting visible illumination light from the second source optical train, and directing the emitted visible illumination light from the second source optical train to illuminate the tissue region of interest in the surgical field on the patient's body;

selectively turning OFF the illumination light source; and receiving, by a receiving optical train while the illumination light source is turned OFF, light signals including the first autofluorescence light emitted from healthy nervous tissue in the tissue region of interest, and optically filtering the received light signals to only pass light signals of wavelengths in the second wavelength range, and optically coupling the optically filtered received light signals into a camera device.

12. The method of claim 11, comprising:

capturing, by the camera device, image data of the optically filtered received light signals including the first autofluorescence light emitted from the healthy nervous tissue and received by the receiving optical train.

13. The method of claim 12, comprising:

displaying an image real-time on a display screen based on the captured image data, showing the healthy nervous tissue contrasted to healthy non-nervous tissue surrounding the healthy nervous tissue in the tissue region of interest in the surgical field on the patient's body.

14. The method of claim 12, comprising:

performing image processing of the captured image data from the camera device;

overlaying an image of the first autofluorescence light emitted from the healthy nervous tissue and an image of surrounding healthy non-nervous tissue in the tissue region of interest to create a composite image of the tissue region of interest; and displaying the composite image real-time on a display screen showing the healthy nervous tissue contrasted to healthy non-nervous tissue surrounding the healthy nervous tissue in the tissue region of interest in the surgical field on the patient's body.

15. The method of claim 11, wherein the first wavelength range is from 382 nm to 392 nm.

16. A method for a nervous tissue imaging system, the method comprising:

selectively turning ON an excitation light source;

optically coupling excitation light, from the excitation light source into a source optical train, and optically filtering the excitation light to only pass excitation light signals in a first wavelength range from 382 nm to 392 nm, and directing emitted excitation light from the source optical train to uniformly illuminate a tissue region of interest causing healthy nervous tissue in the tissue region of interest, in response to being illuminated with the excitation light, to endogenously autofluoresce and emit first autofluorescence light at a first luminance in a second wavelength range from 433 nm to 450 nm;

selectively turning ON an illumination light source;

optically coupling illumination light, from the illumination light source into a second source optical train, and optically filtering the illumination light to only pass illumination light signals of wavelengths outside of the first wavelength range and outside of the second wavelength range, thereby emitting approximately white visible illumination light from the second source optical train, and directing the emitted approximately white visible illumination light from the second source optical train to illuminate the tissue region of interest in the surgical field on the patient's body;

receiving, by a receiving optical train, light signals including the first autofluorescence light emitted from healthy nervous tissue in the tissue region of interest, and optically filtering the received. light signals to only pass light signals of wavelengths in the second wavelength range, and optically coupling the optically filtered received light signals into a camera device;

capturing, by the camera device, image data of the optically filtered received light signals including the first autofluorescence light emitted from the healthy nervous tissue and received by the receiving optical train;

performing image processing of the captured image data from the camera device;

overlaying an image of the first autofluorescence light emitted from the healthy nervous tissue and an image of surrounding healthy non-nervous tissue in the tissue region of interest to create a composite image of the tissue region of interest; and displaying the composite image real-time on a display screen showing the healthy nervous tissue contrasted to healthy non-nervous tissue surrounding the healthy nervous tissue in the tissue region of interest in the surgical field on the patient's body.

* * * * *